(12) United States Patent
Dalbøge et al.

(10) Patent No.: US 6,270,968 B1
(45) Date of Patent: Aug. 7, 2001

(54) METHOD OF PROVIDING A HYBRID POLYPEPTIDE EXHIBITING AN ACTIVITY OF INTEREST

(75) Inventors: Henrik Dalbøge, Virum; Thomas Sandal, Herlev; Markus Sakari Kauppinen, København; Børge Diderichsen, Kobenhavn, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/189,060

(22) Filed: Nov. 5, 1998

Related U.S. Application Data

(63) Continuation of application No. PCT/DK97/00216, filed on May 12, 1997.

(30) Foreign Application Priority Data

May 10, 1996 (DK) .................................................. 0562/96

(51) Int. Cl.[7] .............................. C12Q 1/68; C12P 19/34
(52) U.S. Cl. ............................... 435/6; 435/29; 435/91.2; 435/69.1; 435/455; 435/471; 435/476
(58) Field of Search ............................ 435/6, 91.2, 29, 435/69.1, 455, 471, 476

(56) References Cited

U.S. PATENT DOCUMENTS

| | | | |
|---|---|---|---|
| 5,457,046 | * 10/1995 | Woldike et al. | 435/209 |
| 5,512,478 | * 4/1996 | Orser et al. | 435/252.33 |
| 5,780,225 | * 7/1998 | Wigler et al. | 435/6 |
| 5,849,491 | * 12/1998 | Radomski et al. | 435/6 |

FOREIGN PATENT DOCUMENTS

| | | |
|---|---|---|
| 0 368 684 | 5/1990 | (EP) . |
| WO 91/17243 | 11/1991 | (WO) . |
| WO 91/17244 | 11/1991 | (WO) . |
| WO 93/11249 | 6/1993 | (WO) . |
| WO 94/07998 | 4/1994 | (WO) . |
| WO 96/29397 | 9/1996 | (WO) . |

OTHER PUBLICATIONS

Okuta et al., Gene 212, 221–228 (1998).*
Heussler et al., Mol. Biochem. Parasit. 64, 11–23 (1994).*
Repaske et al., J. Biol. Chem. 267(26), 18683–18688 (1992).*
Sarantopoulos et al., Journal of Immunology, vol. 152, No. 11, pp. 5344–5351 (Jun. 1, 1994).
Henrissat et al., Journal Biochem., vol. 280, pp. 309–316 (1991).
Smalla et al., Journal of Applied Bacteriol., vol. 74, pp. 78–85 (1993).
Stein et al., Journal Bacteriol., vol. 178, No. 3, pp. 591–599 (Feb. 1996).
Embleton et al., Nucleic Acids Research, vol. 20, No. 15, pp. 3831–3837 (1992).

* cited by examiner

*Primary Examiner*—Kenneth R. Horlick
(74) *Attorney, Agent, or Firm*—Elias J. Lambins, Esq.; Jason I. Garbell, Esq.

(57) ABSTRACT

A method for providing a hybrid polypeptide having an activity of interest, by i) performing PCR amplification using an uncharacterized DNA sample and oligonucleotide primers with homology to one or more known genes encoding a polypeptide exhibiting said activity of interest, to obtain one or more PCR products, ii) linking the obtained PCR products to a 5' structural gene sequence and a 3' structural gene sequence, wherein the 5' and 3' structural gene sequences are derived from one or more genes encoding a polypeptide exhibiting said activity of interest, to form hybrid DNA sequences, iii) expressing the resulting hybrid DNA sequences, and iv) screening the hybrid polypeptides to identify a sequence encoding a polypeptide exhibiting said activity of interest or a related activity.

33 Claims, 5 Drawing Sheets

```
PULPZYME_L    1  ----------MRQK---------------KLTFILAFLVCFA  17
XYNA_BACCI    1  -------MFKFKKN-----------------------FLV  10
XYNA_BACPU    1  --------MNLRKL--------------------------  19
XYNA_BACST    1  --------MKLKKK------------------------MLT   9
XYNA_BACSU    1  -------MFKFKKN-----------------------FLV  10
XYNA_CLOAB    1  ---------MLRRK---------------VIFTVLATLVMTS 18
XYNA_CLOSR    1  ------MKRKVKKM---------------AAMATSIIMAIMI 21
XYNA_STRLI    1  --MNLLVQPRRRRR-GPVTLLVR-----SAWAVALAALAALM 34
XYNA_STRLI    1  MQQDGTQQDRIKQSPAPLNGMSRRGFLGGAGTLALATASGLL 42

PULPZYME_L   18  LTLPAE---------------------------------IIQAQ  28
XYNA_BACCI   11  GLSAAL-----------------------------------MSI  19
XYNA_BACPU   20  LTAVP-----------------------------------AHAR  28
XYNA_BACST   10  LLLTAS-----------------------------------MSF  18
XYNA_BACSU   11  GLSAAL-----------------------------------MSI  19
XYNA_CLOAB   19  LTIVDNTAFAATNLNTTESTFSKEVLSTQKTYSAFNTQAAPK  60
XYNA_CLOSR   22  ILHSIP----------------------------------VLAGR 32
XYNA_STRLI   35  LPGTAQ-----------------------------------AOT  43
XYNA_STRLI   43  EPGTAH-----------------------------------AAT  51

PULPZYME_L   29  IVTDNSIGNHDGYDYEFWKDSGGSGTMLNHGGTFSAQWNNV  70
XYNA_BACCI   20  SLFSATASAASTDYWQNWTDGGGIVNAVNGSGGNYSVNWSNT  61
XYNA_BACPU   29  TITNNEMGNHSGYDYELWKDYG-NTSMTLNNGGAFSAGWNNI  69
XYNA_BACST   19  GLFGATSSAA-TDYWQYWTDGGGMVNAVNGPGGNYSVTWQNT  59
XYNA_BACSU   20  SLFSATASAASTDYWQNWTDGGGIVNAVNGSGGNYSVNWSNT  61
XYNA_CLOAB   61  TITSNEIGVNGGYDYELWKDYG-NTSMTLKNGGAFSCQWSNI 101
XYNA_CLOSR   33  IIYDNETGTHGGYDYELWKDYG-NTIMELNDGGTFSCQWSNI  73
XYNA_STRLI   44  VVTTNQEGTNNGYYYSFWTDSQGTVSMNMGSGGQYSTSWRNT  65
XYNA_STRLI   52  TITTNQTGT-DGMYYSFWTDGGGSVSMTLNGGGSYSTQWTNC  92

PULPZYME_L   71  NNILFRKGKKFNETQHQQVGNMSINYGANFQ-PNGNAYLCV 111
XYNA_BACCI   62  GNFVVGKGWTTGS-------PFRTINYNAGVWAPNGNGYLTL  96
XYNA_BACPU   70  GNALFRKGKKFDSTRTHHQLGNISINYNASFN-PGGNSYLCV 110
XYNA_BACST   60  GNFVVGKGWTVGS-------PNRVINYNAGIWEPSGNGYLTL  94
XYNA_BACSU   62  GNFVVGKGWTTGS-------PFRTINYNAGVWAPNGNGYLTL  96
XYNA_CLOAB  102  GNALFRKGKKFNDTQTYKQLGNISVNYDCNYQ-PYGNSYLCV 142
XYNA_CLOSR   74  GNALFRKGRKFNSDKTYQELGDIVVEYGCDYN-PNGNSYLCV 114
XYNA_STRLI   86  GNFVAGKGWANG-------GRRTVQYSGSFN-PSGNAYLAL 118
XYNA_STRLI   93  GNFVAGKGWSTGD-------GN--VRYNGYFN-PVGNGYGCL 124
```

FIG 2A

```
PULPZYME_L  112  YGWTVDPLVEYYIVDSWGNWRPPGATPKGTITVEGG-TYDIY  152
XYNA_BACCI   97  YGWTRSPLIEYYVVDSWGTYRPTGTYKG-TVKSEGG-TYDIY  136
XYNA_BACPU  111  YGWTQSPLAEYYIVDSWGTYRPTG-AYKGSFYAEGG-TYDIY  150
XYNA_BACST   95  YGWTRNALIEYYVVDSWGTYRATGNYESGTVNSEGG-TYDIY  135
XYNA_BACSU   20  YGWTRSPLIEYYVVDSWGTYRPTGTYKG-TVKSEGG-TYDIY  136
XYNA_CLOAB  143  YGWTSSPLVEYYIVDSWGSWRPPGGTSKGTITVEGG-IYDIY  183
XYNA_CLOSR  115  YGWTRNPLVEYYIVESWGSWRPPGATPKGTITQWMAGTYEIY  156
XYNA_STRLI  119  YGWTSNPLVEYYIVDNWGTYRPTGEYKG-TVTSEGG-TYDIY  158
XYNA_STRLI  125  YGWTSNPLVEYYIVDNWGSYRPTGTYKG-TVSSEGG-TYDIY  164

PULPZYME_L  153  ETLRVNQPSIKG-IATFKQYWSVRRSKRTSG---TISVSNHF  190
XYNA_BACCI  137  TTTRYNAPSIDGDRTTFTQYWSVRQSKRPTGSNATITFTNHV  178
XYNA_BACPU  151  ETTRVNQPSIIG-IATFKQYWSVRQTKRTSG---TVSVSAHF  188
XYNA_BACST  136  TTMRYNAPSIDG-TQTFQQFWSVRQSKRPTGSNVSITFSNHV  176
XYNA_BACSU  137  TTTRYNAPSIDGDRTTFTQYWSVRQSKRPTGSNATITFSNHV  178
XYNA_CLOAB  184  ETTRINQPSIQG-NTTFKQYWSVRRTKRTSG---TISVSKHF  221
XYNA_CLOSR  157  ETTRVNQPSIDG-TATFQQYWSVRTSKRTSG---TISVTEHF  194
XYNA_STRLI  159  KTTRVNKPSVEG-TRTFDQYWSVRQSKRTGG---TITTGNHF  196
XYNA_STRLI  165  QTTRYNAPSVEG-TKTFQQYWSVRQSKVTSGS-GTITTGNHF  204

PULPZYME_L  191  RAWENLGMNMG-KMYEVALTVEGYQSSGSANVYSNTLRINGN  231
XYNA_BACCI  179  NAWKSHGMNLGSNWAYQVMATEGYQSSGSSNVTVW-------  213
XYNA_BACPU  189  RKWESLGMPMG-KMYETAFTVEGYQSSGSANVMTNQLFIGN-  228
XYNA_BACST  177  NAWRSKGMNLGSSWAYQVLATEGYQSSGRSNVTVW-------  211
XYNA_BACSU  179  NAWKSHGMNLGSNWAYQVMATEGYQSSGSSNVTVW-------  213
XYNA_CLOAB  222  AAWESKGMPLG-KMHETAFNIEGYQSSGKADVNSMSINIGK-  261
XYNA_CLOSR  195  KQWERMGMRMG-KMYEVALTVEGYQSSGYANVYKNEIRIGAN  235
XYNA_STRLI  197  DAWARAGMPLGNFSYYMIMATEGYQSSGTSSINVGGTGGGDS  238
XYNA_STRLI  205  DAWARAGMNMGQFRYYMIMATEGYQSSGSSNITVSG------  240
```

FIG 2B

```
PULPNS8-11    1  MRQKKLTFILAFLVCFALTLPAEIIQAQIVTDN   33
PULPZYME_L    1  MRQKKLTFILAFLVCFALTLPAEIIQAQIVTDN   33

PULPNS8-11   34  SIGNHDGYDYEFWKDSGGSGTMILNHGGTFSAQ   66
PULPZYME_L   34  SIGNHDGYDYEFWKDSGGSGTMILNHGGTFSAQ   66

PULPNS8-11   67  WNNVNNILFRKGKKFNETQTHQQVGNMSINYGA   99
PULPZYME_L   67  WNNVNNILFRKGKKFNETQTHQQVGNMSINYGA   99

PULPNS8-11  100  NFQPNGNAYLCVYGWTVDPLVEYYIVDSWGNWR  132
PULPZYME_L  100  NFQPNGNAYLCVYGWTVDPLVEYYIVDSWGNWR  132

PULPNS8-11  133  PPGATPKGTITVDGGTYDIYKHQQVNQPSIQGT  165
PULPZYME_L  133  PPGATPKGTITVDGGTYDIYETLRVNQPSIKGI  165

PULPNS8-11  168  ATFNQYWSIRQSKRTSGTVTTANHFNAWAALGM  198
PULPZYME_L  168  ATFKQYWSVRRSKRTSGTISVSNHFRAWENLGM  198

PULPNS8-11  199  NMGAFNYQILVTEGYQSTGSANVYSNTLRINGN  231
PULPZYME_L  199  NMGKMYEVALTVEGYQSSGSANVYSNTLRINGN  231

PULPNS8-11  232  PLSTISNDKSITLDKNN                  248
PULPZYME_L  232  PLSTISNDKSITLDKNN                  248
```

FIG 3

METHOD OF PROVIDING A HYBRID POLYPEPTIDE EXHIBITING AN ACTIVITY OF INTEREST

CROSS-REFERENCE TO RELATED APPLICATIONS

This application is a continuation of PCT/DK97/00216 filed May 12, 1997 and claims priority under 35 U.S.C. 119 of Danish application 0562/96 filed May 10, 1996, the contents of which are fully incorporated herein by reference.

FIELD OF THE INVENTION

The present invention relates to a method of providing novel DNA sequences encoding a polypeptide with an activity of interest, novel DNA sequences provided according to the method of the invention, polypeptides with an activity of interest encoded by novel DNA sequences of the invention.

BACKGROUND OF THE INVENTION

The advent of recombinant DNA techniques has made it possible to select single protein components with interesting properties and produce them on a large scale. This represents an improvement over the previously employed production process using microorganisms isolated from nature and producing a mixture of proteins which would either be used as such or separated after the production step.

Since the traditional methods were rather time-consuming, more rapid and less cumbersome methods were developed.

A such technique is described in WO 93/11249 (Novo Nordisk A/S).

The method described in WO 93/11249 comprises the steps of:
a) cloning, in suitable vectors, a DNA library from an organism suspected of producing one or more proteins of interest;
b) transforming suitable yeast host cells with said vectors;
c) culturing the host cells under suitable conditions to express any protein of interest encoding by a clone in the DNA library; and
d) screening for positive clones by determining any activity of a protein expressed in step c).

According to this method it is necessary to prepare a DNA library, comprising complete genes encoding polypeptides with activities of interest. Such a library has traditionally been made on mRNA isolated from micro-organisms which has been cultivated and isolated.

As it is only possible with known methods to cultivate about 2% of the microorganisms known today (i.e. cultivable microorganisms), genes encoding polypeptides from a huge number of microorganisms (i.e. un-cultivable microorganisms) are generally difficult to identify and clone on the basis of screening technologies used today, such as the above mentioned.

SUMMARY OF THE INVENTION

It is the object of the present invention to provide a method for providing a novel DNA sequence encoding a polypeptide with an activity of interest from micro-organisms without having to cultivate and isolate said micro-organisms.

In the first aspect the invention relates to a method of providing novel DNA sequences encoding a polypeptide with an activity of interest, comprising the following steps:

i) PCR amplification of said DNA with PCR primers with homology to (a) known gene(s) encoding a polypeptide with an activity of interest,
ii) linking the obtained PCR product to a 5' structural gene sequence and a 3' structural gene sequence,
iii) expressing said resulting hybrid DNA sequence,
iv) screening for hybrid DNA sequences encoding a polypeptide with said activity of interest or related activity,
v) isolating the hybrid DNA sequence identified in step iv)

Further, the invention also relates novel DNA sequences provided according to the method of the invention and polypeptides with an activity of interest encoded by said novel DNA sequences of the invention.

BRIEF DESCRIPTION OF THE DRAWING

(in FIG. 1)
PCR with primers ab and cd to amplify unknown core genes with an activity of interest.
PCR with primers e and $a_{rc}$ to obtain the N-terminal part of the known gene.
PCR with primers $d_{rc}$ and f to obtain the C-terminal part of the known gene.
2.
(in FIG. 1)
SOE-PCR with primers e and f to link the unknown core gene sequence with the known N- and C-terminal gene sequences and introduction of EcoRI and SalI restriction recognition sites.
3. Restriction enzyme digestion followed by ligation of the novel sequence into an expression vector and transformation into a host cell. Screening of clones expressing the produced gene product with the activity of interest.

FIG. 2 shows a part of an alignment of prokaryote xylanases belonging to glycosyl hydrolases family 11.

FIG. 3 shows an alignment of the translated DNA sequences of Pulpzyme® (SEQ ID NO 2) and the novel gene sequence found in soil, respectively.

Figure 1:
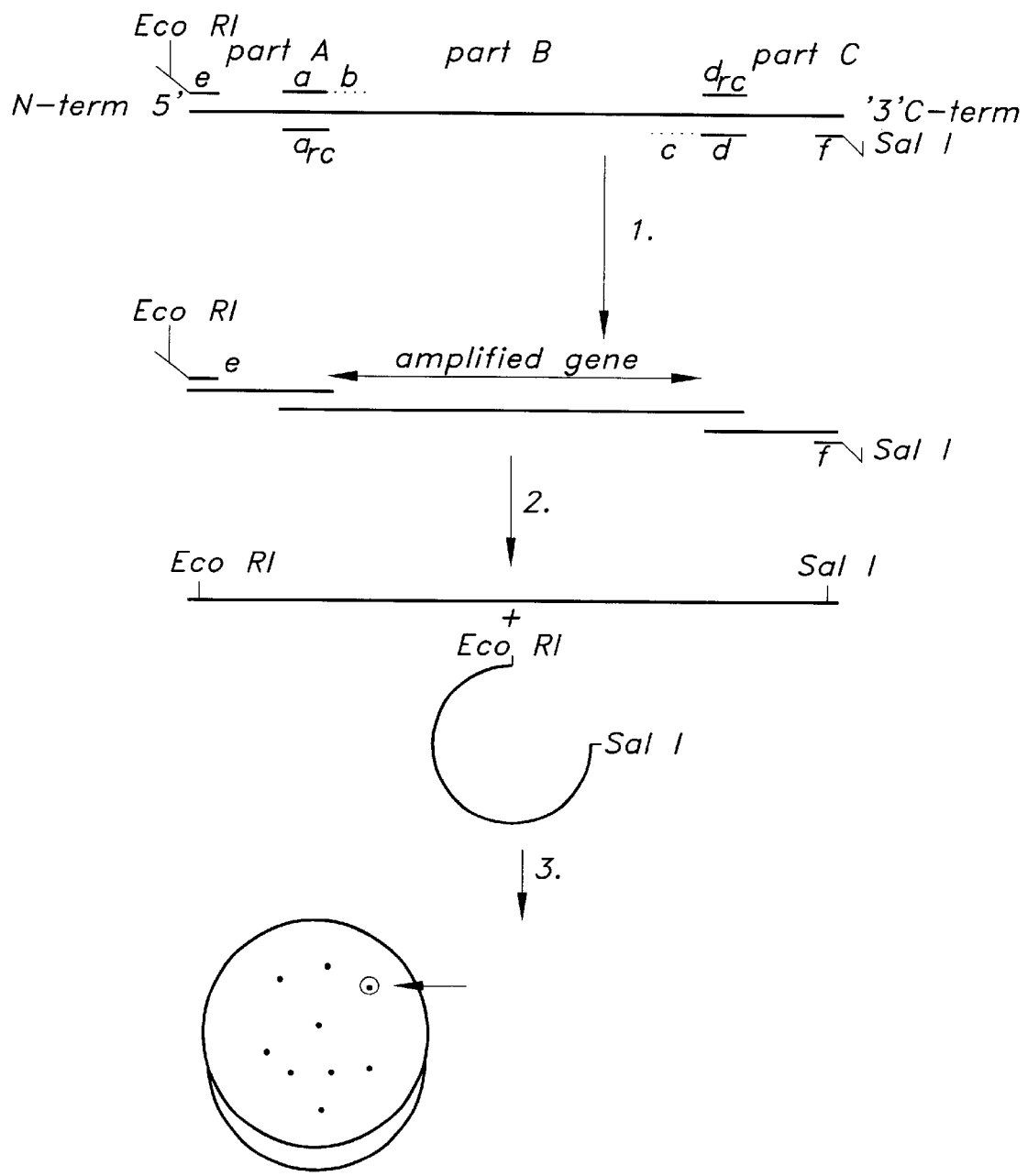
FIG. 1 shows the cloning strategy of novel hybrid enzyme sequences.
 a is an exact N-terminal consensus primer
 $a_{rc}$ is the reverse and complement primer to a
 b is a degenerated homologous N-terminal primer
 c is a degenerated homologous C-terminal primer
 d is an exact C-terminal consensus primer
 $d_{rc}$ is a reverse and complement of d
 f is an exact reverse and complement C-terminal primer extended with a sequence which includes a SalI restriction recognition site.
 e is an exact N-terminal primer extended with a sequence which includes an EcoRI restriction recognition site.
1.

Using Pulpzyme® (SEO ID NO 1) as the starting sequence: "1" indicated the first nucleotide of the novel hybrid gene provided according to the invention, "433" and "631" the start and end of the part constituted by the unknown gene sequence and "741" the last nucleotide of the novel hybrid gene sequence.

DEFINITIONS

Prior to discussing this invention in further detail, the following terms will first be defined.

"Homology of DNA sequences or polynucleotides" In the present context the degree of DNA sequence homology is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711)(Needleman, S. B. and Wunsch, C. D., (1970), Journal of Molecular Biology, 48, 443–453).

"Homologous": The term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later (vide infra).

Using the computer program GAP (vide supra) with the following settings for DNA sequence comparison: GAP creation penalty of 5.0 and GAP extension penalty of 0.3, it is in the present context believed that two DNA sequences will be able to hybridize (using low stringency hybridization conditions as defined below) if they mutually exhibit a degree of identity preferably of at least 70%, more preferably at least 80%, and even more preferably at least 85%.

"heterologous": If two or more DNA sequences mutually exhibit a degree of identity which is less than above specified, they are in the present context said to be "heterologous". "Hybridization:" Suitable experimental conditions for determining if two or more DNA sequences of interest do hybridize or not is herein defined as hybridization at low stringency as described in detail below.

A suitable experimental low stringency hybridization protocol between two DNA sequences of interest involves pre-soaking of a filter containing the DNA fragments to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 $\mu$g/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6–13), $^{32}$P-dCTP-labeled (specific activity>1×10$^9$ cpm/$\mu$g) probe (DNA sequence) for 12 hours at ca. 45° C. The filter is then washed twice for 30 minutes in 2×SSC, 0.5% SDS at least 50° C., more preferably at least 55° C., and even more preferably at least 60° C. (high stringency).

Molecules to which the oligonucleotide probe hybridizes under these conditions are detected using a x-ray film.

"Alignment": The term "alignment" used herein in connection with a alignment of a number of DNA and/or amino acid sequences means that the sequences of interest is aligned in order to identify mutual/common sequences of homology/identity between the sequences of interest. This procedure is used to identify common "conserved regions" (vide infra), between sequences of interest. An alignment may suitably be determined by means of computer programs known in the art, such as ClusterW or PILEUP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453).

"Conserved regions:" The term "conserved region" used herein in connection with a "conserved region" between DNA and/or amino acid sequences of interest means a mutual common sequence region of the sequences of interest, wherein there is a relatively high degree of sequence identity between the sequences of interest. In the present context a conserved region is preferably at least 10 base pairs (bp)/3 amino acids(a.a), more preferably at least 20 bp/7 a.a., and even more preferably at least 30 bp/10 a.a.

Using the computer program GAP (Program Manual for the Wisconsin Package, Version 8, August 1994, Genetics Computer Group, 575 Science Drive, Madison, Wis., USA 53711)(Needleman, S. B. and Wunsch, C. D., (1970), Journal of Molecular Biology, 48, 443–453) (vide supra) with the following settings for DNA sequence comparison: GAP creation penalty of 5.0 and GAP extension penalty of 0.3, the degree of DNA sequence identity within the conserved region is preferably of at least 80%, more preferably at least 85%, more preferably at least 90%, and even more preferably at least 95%.

"Sequence overlap extension PCR reaction (SOE-PCR)": The term "SOE-PCR" is a standard PCR reaction protocol known in the art, and is in the present context defined and performed according to standard protocols defined in the art ("PCR A practical approach" IRL Press, (1991)).

"primer": The term "primer" used herein especially in connection with a PCR reaction is an oligonucleotide (especially a "PCR-primer") defined and constructed according to general standard specification known in the art ("PCR A practical approach" IRL Press, (1991)).

"A primer directed to a sequence:" The term "a primer directed to a sequence" means that the primer (preferably to be used in a PcR reaction) is constructed so it exhibits at least 80% degree of sequence identity to the sequence part of interest, more preferably at least 90% degree of sequence identity to the sequence part of interest, which said primer consequently is "directed to". The primer is designed in order to specifically anneal at the region at a given temperature it is directed towards. Especially identity at the 3' end of the primer is essential for the function of the polymerase, i.e. the ability of a polymerase to extend the annealed primer.

"Polypeptide" Polymers of amino acids sometimes referred to as protein. The sequence of amino acids determines the folded conformation that the polypeptide assumes, and this in turn determines biological properties such as activity. Some polypeptides consist of a single polypeptide chain (monomeric), whilst other comprise several associated polypeptides (multimeric). All enzymes and antibodies are polypeptides.

"Enzyme" A protein capable of catalysing chemical reactions. Specific types of enzymes are a) hydrolases including amylases, cellulases and other carbohydrases, proteases, and lipases, b) oxidoreductases, c) Ligases, d) Lyases, e) Isomerases, f) Transferases, etc. Of specific interest in relation to the present invention are enzymes used in detergents, such as proteases, lipases, cellulases, amylases, etc.

"known sequence" is the term used for the DNA sequences of which the full length sequence has been sequenced or at least the sequence of one conserved regions is known.

"unknown sequence" is the term used for the DNA sequences amplified directly from uncultivated microorganisms comprised in e.g. a soil sample used as the starting materia. "Full length DNA sequence" means a structural gene sequence encoding a complete polypeptide with an activity of interest.

"un-cultivated" means that the micro-organism comprising the unknown DNA sequence need not be isolated (i.e. to provide a population comprising only identical micro-organisms) before amplification (e.g. by PCR).

The term "an activity of interest" means any activity for which screening methods is known.

The term "un-cultivable micro-organisms" defined micro-organisms which can not be cultivated according to methods know in the art.

The term "DNA" should be interpreted as also covering other polynucleotide sequences including RNA.

The term "linking" sequences means effecting a covalent binding of DNA sequences.

The term "hybrid sequences" means sequences of different origin merged together into one sequence.

The term "structural gene sequence" means a DNA sequence coding for a polypeptide with an activity.

The term "natural occurring DNA" means DNA, which has not been subjected to biological or biochemical mutagenesis. By biological mutagenesis is meant "in vivo" mutagenesis, i.e. propagation under controlled conditions in a living organism, such as a "mutator" strain, in order to create genetic diversity. By biochemical mutagenesis is meant "in vitro" mutagenesis, such as error-prone PCR, oligonucleotide directed site-specific or random mutagenesis etc.

DETAILED DESCRIPTION OF THE INVENTION

It is the object of the present invention to provide a method for providing novel DNA sequences encoding polypeptides with an activity of interest from micro-organisms without having to cultivate said micro-organisms.

The inventors of the present invention have found that PCR-screening using primers designed on the basis of known homologous region, such as conserved regions, can be used for providing novel DNA sequences. Despite the fact that known homologous regions, such as conserved regions, are used for primer designing a vast number of unknown DNA sequences have been provided. This will be described in the following and illustrated in the Examples.

The DNA sequences provided are full length hybrid structural gene sequences encoding complete polypeptides with an activity of interest made up of one unknown sequence and one or two known sequences.

According to the invention it is essential to identify at least two homologous regions, such as conserved regions, in known gene sequences with the activity of interest. One or two selected known structural gene sequence(s) is(are) used as templates (i.e. as starting sequence(s)) for finding and constructing novel DNA structural gene sequences with an activity of interest.

Said homologous regions, such as conserved regions, can be identified by alignment of polypeptides with the activity of interest and may e.g. be made by the computer program ClustalW or other similar programs available on the market.

One Known Structural Gene as the Starting Sequence

In the case of using one known structural gene sequence as the starting sequence it will typically be comprised in a plasmid or vector or the like. A part of the sequence between the two identified homologous regions, such as conserved regions, are deleted to avoid contamination by the wild-type structural gene.

The known DNA sequence, with the homologous regions, such as conserved regions, placed at the ends, are linked to an unknown DNA sequence amplified directly or indirectly from a sample comprising micro-organisms.

The identified homologous regions, such as conserved regions, must have a suitable distance from each other, such as 10 or more base pairs in between. It is preferred to use homologous regions, such as conserved regions, placed in each end of the known structural full length gene.

However, if knowledge about a specific function (e.g. active site) of a domain (i.e. part of the structural gene sequence) is available it may be advantageous to used conserved regions placed in proximity of and on each side said domain as basis for the PCR amplification to provide novel DNA sequences according to the invention which will be described below in details.

Two Known Genes as Starting Sequences

In the case of using two known structural genes as the stating sequences at least one homologous region, such as conserved region, should be identified in each of the two sequences within the polypeptide coding region.

In both case (i.e. one or two known genes as starting sequences) the homologous regions, such as conserve regions, should preferably be situated at each end of the structural gene(s) (i.e. the sequences encoding the N-terminal end (i.e. named Part A on FIG. 4) and the C-terminal end, respectively (i.e. named Part C on FIG. 4) of the known part of the hybrid polypeptide In the first aspect the invention relates to a method for providing novel DNA sequences encoding polypeptides with an activity of interest comprises the following steps:

i) PCR amplification of said DNA with PCR primers with homology to (a) known gene(s) encoding a polypeptide with an activity of interest, ii) linking the obtained PCR product to a 5' structural gene sequence and a 3' structural gene sequence, iii) expressing said resulting hybrid DNA sequence, iv) screening for hybrid DNA sequences encoding a polypeptide with said activity of interest or related activity, v) isolating the hybrid DNA sequence identified in step iv)

In step i) the part between the corresponding homologous regions, such as conserved regions, of the unknown structural gene are amplified.

In an embodiment the PCR amplification in step i) is performed using naturally occurring DNA or RNA as template.

In anither embodiment the micro-organism has not been subjected to "in vitro" selection.

The PCR amplification may be performed on a sample containing DNA or RNA from un-isolated micro-organisms. According to the invention no prior knowledge about the unknown sequence is required.

In an embodiment of the invention said 5' and 3' structural gene sequences originate from two different known structural gene sequences encoding polypeptides having the same activity or related activity.

The 5' structural gene sequence and the 3' structural gene sequence may also originate from the same known structural gene encoding a polypeptide with the activity of interest or from two different known structural gene sequences encoding polypeptides having different activities. In the latter case it is preferred that at least one of the starting sequences originates from a known structural gene sequence encoding a polypeptide with the activity of interest.

In a preferred embodiment of the method of the invention the known structural gene is situated in a plasmid or a vector. In said case the method comprises the following steps:

i) PCR amplification of DNA from micro-organisms with PCR primers being homologous to conserved regions of a known gene encoding a polypeptide with an activity of interest, ii) cloning the obtained PCR product into a gene encoding a polypeptide having said activity of interest, where said gene is not identical to the gene from which the PCR product is obtained, which gene is situated in an expression vector, iii) transforming said expression vector into a suitable host cell, iiia) culturing said host cell under suitable conditions, iv) screening for clones comprising a DNA sequence originated from the PCR amplification in step i) encoding a polypeptide with said activity of interest or a related activity, v) isolating the DNA sequence identified in step iv).

According to this embodiment one known structural gene sequence is used as the starting sequence. It is to be understood that the PCR product obtained in step i) is cloned into a known gene where a part of the DNA sequence, between the conserved regions, is deleted (i.e. cut out) or in an other way substituted with the PCR product. The deleted part of the known gene comprised in the vector may have any suitable size, typically between 10 and 5000 bp, such as from between 10 to 3000 bp.

A general problem is that, when amplifying DNA sequences encoding polypeptides with an activity by PCR, the obtained PCR product (i.e. being a part of an unknown gene) does not normally encode a polypeptide with the desired activity of interest.

Therefore, according to the invention the complete full length structural gene, encoding a functional polypeptide, is provided by cloning (i.e. by substituting) the PCR product of the unknown structural gene into the known gene situated on the expression vector.

It should be emphasised that the DNA mentioned in step i), to be PCR amplified, need not to comprise a complete gene encoding a functional polypeptide. This is advantageous as only a smaller region of the DNA of the micro-organism(s) in question need to be amplified.

The novel DNA sequences obtained according to the invention consist of the PCR product merged or linked into the known gene, having a number of nucleotides between the conserved regions deleted. The PCR product is inserted into the known gene between the two ends of the cut open vector by overlapping homologous regions of about 10 to 200 bp at each end of the vector.

The resulting novel hybrid DNA sequences constitute complete full length genes comprising the PCR product and encodes a polypeptide with the activity of interest.

It is to be understood that it is not absolutely necessary to delete a part of the known gene sequence. However, if a part of the known gene sequence is not deleted re-ligation results in that the wild-type activity of the known gene is regained and thus give a high number of wild-type background clones, which would make the screening procedure more time consuming and cumbersome.

The PCR amplification in step i) can be performed on both cultivable and uncultivable micro-organisms by directly or indirectly amplification of DNA from the genomic material of the micro-organisms in the environment (i.e. directly or indirectly from the sample taken).

The Micro-organisms

The micro-organisms from which the unknown DNA sequences are derived may be micro-organisms which cannot today be cultivated. This is possible as the DNA sequences can be amplified by PCR without the need first to cultivate and isolate the micro-organisms comprising the unknown DNA sequence(s).

It is however to be understood that the method of the invention can also be used for providing novel DNA sequences derived from micro-organisms which can be cultivated.

Therefore the method of the invention can be performed on both cultivable and un-cultivable organisms as the micro-organisms in question do not, according to the method of the invention, need to be cultivated and isolated from, e.g. the soil sample, comprising micro-organisms.

Starting Material

The starting material, i.e. the sample comprising micro-organisms with the target unknown DNA sequences, may for instance be an environmental samples of plant or soil material, animal or insect dung, insect gut, animal stomach, a marine sample of sea or lake water, sewage, waste water, etc., comprising one or, as in most case, a vast number of different cultivable and/or un-cultivable micro-organisms.

If the genomic material of the micro-organisms are readily accessible the PCR amplification may be performed directly on the sample. In other cases a pre-purification and isolation procedure of the genomic material is needed.

Smalla et al. (1993), J. Appl. Bacteriol 74, p. 78–85; Smalla et al. (1993), FEMS Microbiol Ecol 13, p. 47–58, describes how to extract DNA directly from micro-organisms in the environment (i.e. the sample).

Borneman et al. (1996), Applied and Environmental Microbiology, 1935–1943, describes a method for extracting DNA from soils.

A commercially available kit for isolating DNA from environmental samples, such as e.g. soils, can be purchased from BIO 101 under the tradename FastDNA® SPIN Kit.

Seamless™ Cloning kit (cataloge no. Stratagene 214400) is a commercial kit suitable for cloning of any DNA fragment into any desired location e.g. a vector, without the limitation of naturally occurring restriction sites.

PCR amplification of DNA and/or RNA of micro-organisms in the environment is described by Erlich, (1989), PCR Technology. Principles and Applications for DNA Amplification, New York/London, Stockton Press; Pillai, et al., (1991), Appl. Environ. Microbiol, 58, p. 2712–2722)

Other methods for PCR amplifying microbial DNA directly from a sample is described in Molecular Microbial Ecology Manual, (1995), Edited by Akkermans et al. A suitable method for microbial DNA from soil samples is described by Jan Dirk van Elsas et al., (1995), Molecular Microbial Ecology Manual 2.7.2, p. 1–10.

Stein et al., (1996), J. Bacteriol., Vol. 178, No. 2, p. 591–599, describes a method for isolating DNA from un-cultivated prokaryotic micro-organisms and cloning DNA fragments therefrom.

The PCR primers being homologous to conserved regions of the known gene encoding a polypeptide with an activity of interest are synthesized according to standard methods known in the art (see for instance EP 684 313 from Hoffmann-La Roche AG) on the basis of knowledge to conserved regions in the polypeptide with the activity of interest.

Said PCR primers may be identical to at least a part of the conserved regions of the known gene. However, said primers may advantageously be synthisized to differ in one or more positions.

Further, a number of different PCR primers homologous to the conserved regions may be used at the same time in step i) of the method of the invention.

The cultivable or uncultivable micro-organisms may be both prokaryotic organisms such as bacteria, or eukaryotic organisms including algae, fungi and protozoa.

Examples of un-cultivable organisms include, without being limited thereto, extremophiles and plantonic marine organisms etc.

The group of cultivable organisms include bacteria, fungal organisms, such as filamentous fungi or yeasts.

In the case of using DNA from cultivable organisms the PCR amplification in step i) may be performed on one or more polynucleotides comprised in a vector, plasmid or the like, such as on a cDNA library.

Specific examples of "an activity of interest" include enzymatic activity and anti-microbial activity.

In a preferred embodiment of the invention the activity of interest is an enzymatic activity, such as an activity selected from the group comprising of phosphatases oxidoreductases (E.C. 1), transferases (E.C. 2); hydrolases (E.C. 3), such as esterases (E.C. 3.1), in particular lipases and phytase; such as glucosidases (E.C. 3.2), in particular xylanase, cellulases, hemicellulases, and amylase, such as peptidases (E.C. 3.4), in particular proteases; lyases (E.C. 4); isomerases (E.C. 5); ligases (E.C. 6).

The host cell used in step iii) may be any suitable cell which can express the gene encoding the polypeptide with the activity of interest. The host cells may for instance be a yeast, such as a strain of saccharomyces, in particular *Saccharomyces cerevisiae*, or a bacteria, such as a strain of Bacillus, in particular of *Bacillus subtilis*, or a strain *Escherichia coli*.

Clones found to comprise a DNA sequence originated from the PCR amplification in step i) may be screened for any activity of interest. Examples of such activities include enzymatic activity, anti-microbial activity or biological activities.

The polypeptide with the activity of interest may then be tested for a desired performance under specific conditions and/or in combination with e.g. chemical compounds or agent. In the case where the polypeptide is an enzyme e.g. the wash performance, textile dyeing, hair dyeing or bleaching properties, effect in feed or food may be assayed to identify polypeptides with a desired property.

Identification of Conserved Regions of Prokaryote Xylanases

FIG. 2 shows an alignment of prokaryote xylanases from the family 11 of glycosyl hydrolases (B. Henrissat, Biochem J, 280:309–316 (1991)). There are several region where the amino acids are identical or almost identical, i.e. conserved regions.

Examples of homologous regions or conserved regions in prokaryotic xylanases from family 11 of glycosyl hydrolases (B. Henrissat, (1991), Biochem J 280:309–316) are the sequence "DGGTYDIY" (SEQ ID NO 3) position 145–152, "EGYQSSG" (SEQ ID NO. 4) position 200–206 in the upper polypeptide shown in FIG. 2.

Based on e.g. said regions degenerated PCR primers can be designed. These degenerated PCR primers can amplify unknown DNA sequences coding for polypeptides (i.e. referred to as PCR products below) which are homologous to the known polypeptide(s) in question (i.e. SEQ ID NO 2) flanked by the conserved regions.

The PCR products obtained can be cloned into a plasmid and sequenced to check if they contain conserved regions and are homologous to the known structural gene sequence (s).

A homologous PCR product is however not a guarantee that the sequence code for a part of a polypeptide having the desired activity of interest.

Therefore, according to the method of the invention one or more steps selecting DNA sequences encoding polypeptides having the activity of interest follow the construction of the novel hybrid DNA sequences.

The Unknown DNA Sequences

When method of the invention is performed on DNA from samples of uncultivated organisms it is advantageous to screen for gene products with the activity of interest.

A suitable method for doing this is to link the PCR products with a 5' sequence upstream the first conserved region DNA sequence and the 3' sequence downstream the second consensus, respectively, from the known gene sequence.

The product of the unknown gene sequence linked to an N-terminal and C-terminal part of a known gene product is then screened for the activity of interest.

The N-terminal and C-terminal parts can originate from the same gene product but it is not a prerequisite for activity. The N-terminal and C-terminal parts may also originate from different gene products as long as they originate from the same polypeptide family e.g. the same glycosyl hydrolases.

A method to link the unknown gene sequence with the known sequences is to clone the PCR product into a known gene, encoding a polypeptide having the activity of interest, which have had the sequences between the conserved regions removed.

Another method is merging the PCR product, the N-terminal part and the C-terminal part by SOE-PCR (splicing by overlap extension PCR) e.g. as shown in FIG. 1 and described in detail in Example 1. Other methods known in the art may also be used.

In a second aspect the invention relates to a novel DNA sequence provided by the method of the invention and the polypeptide encoded by said novel DNA sequence.

MATERIALS AND METHODS

Pulpzyme® is a xylanase derived from Bacillus sp. AC13, NCIMB No. 40482. and is described in WO 94/01532 from Novo Nordisk A/S AZCL Birch xylan (MegaZyme, Australia).

Plasmids:

The Aspergillus expression vector pHD414 is a derivative of the plasmid p775 (described in EP 238 023). The construction of pHD414 is further described in WO 93/11249.

The 43 kD EG V endoglucanase cDNA from *H. insolens* (disclosed in WO 91/17243) is cloned into pHD414 in such a way that the endoglucanase gene is transcribed from the TAKA-promoter. The resulting plasmid is named pCaHj418.

Kits

QIAquick PCR Purification Kit Protocol

Taq deoxy terminal cycle sequencing kit (Perkin Elmer, USA)

AmpliTaq Gold polymerase (Perkin-Elmer, USA)

Micro-organisms

Bacteria electromax DH10B *E. coli* cells (GIBCO BRL)

Fungal Micro-organisms:

Cylindrocarpon sp.: Isolated from marine sample, the Bahamas

Classification: Ascomycota, Pyrenomycetes, Hypocreales unclassified

*Fusarium anguioides* Sherbakoff IFO 4467

Classification: Ascomycota, Pyrenomycetes, Hypocreales, Hypocreaceae

*Gliocladium catenulatum* Gillman & Abbott CBS 227.48

Classification: Ascomycota, Pyrenomycetes, Hypocreales, Hypocreaceae

*Humicola nigrescens* Omvik CBS 819.73
Classification: Ascoinycota, Pyrenomycetes, Sordariales, (fam. unclassified)

*Trichothecium roseum* IFO 5372

Plates

LB-ampicillin plates: 10 g Bacto-tryptone, 5 g Bacto yeast extract, 10 g NaCl, in 1 litre water, 2% agar 0.1% AZCL Birch xylan, 50 microg/ml ampicillin.

Equipment

Applied Biosystems 373A automated sequencer

PCR Amplification

All Polymerase Chain Reactions is carried out under standard conditions as recommended by Perkin-Elmer using AmpliTaq Gold polymerase.

Isolation of Environmental DNA

DNA is isolated from an environmental sample using PastDNA® SPIN Kit for Soil according to the manufacture's instructions.

Methods Used in Example 3

Strains and Growth Conditions

The fungal strains listed above, were streaked on PDA plates containing 0.5% Avicel, and examined under a microscope to avoid obvious mistakes and contaminations. The strains were cultivated in shake flasks (125 rpm and 26° C.) containing 30 ml PD medium (to initiate the growth) and 150 ml of BA growth medium for cellulase induction.

The production of cellulases in culture supernatants (typically after 3, 5, 7 and 9 days of growth) was assayed using 0.1% AZCl-HE-cellulose in a plate assay at pH 3, pH 7 and pH 10. The mycelia were harvested and stored at −80° C.

Preparation of RNase-free Glassware, Tips and Solutions

All glassware used in RNA isolations were baked at +250° C. for at least 12 hours. Eppendorf tubes, pipet tips and plastic columns were treated in 0.1% diethylpyrocarbonate (DEPC) in EtOH for 12 hours, and autoclaved. All buffers and water (except Tris-containing buffers) were treated with 0.1% DEPC for 12 hours at 37° C., and autoclaved.

Extraction of Total RNA

The total RNA was prepared by extraction with guanidinium thiocyanate followed by ultracentrifugation through a 5.7 M CsCl cushion [Chirgwin, (1979) Biochemistry 18, 5294–5299] using the following modifications. The frozen mycelia was ground in liquid N2 to fine powder with a mortar and a pestle, followed by grinding in a precooled coffee mill, and immediately suspended in 5 vols of RNA extraction buffer (4 M GuSCN, 0.5% Na-laurylsarcosine, 25 mM Na-citrate, pH 7.0, 0.1 M β-mercaptoethanol). The mixture was stirred for 30 min. at RT° and centrifuged (20 min., 10,000 rpm, Beckman) to pellet the cell debris. The supernatant was collected, carefully layered onto a 5.7 M CsCl cushion (5.7 M CsCl, 0.1 M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25,000 rpm, RT°, 24 h). After centrifugation the supernatant was carefully removed and the bottom of the tube containing the RNA pellet was cut off and rinsed with 70% EtOH. The total RNA pellet was transferred into an Eppendorf tube, suspended in 500 µl TE, pH 7.6 (if difficult, heat occasionally for 5 min at 65° C.), phenol extracted and precipitated with ethanol for 12 h at −20° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring OD 260/280.

Isolation of Poly(A)+RNA

The poly(A)+RNAs were isolated by oligo(dT)-cellulose affinity chromatography [Aviv, (1972), Proc. Natl. Acad. Sci. U.S.A. 69, 1408–1412]. Typically, 0.2 g of oligo(dT) cellulose (Boehringer Mannheim, Germany) was preswollen in 10 ml of 1×column loading buffer (20 mM Tris-Cl, pH 7.6, 0.5 M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA (1–2 mg) was heated at 65° C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1 M NaCl, 1 mM EDTA, 0.1% SDS), followed by elution of the poly(A)+RNA with 3 vols of elution buffer (10 mM Tris-Cl, pH 7.6, 1 mM EDTA, 0.05% SDS) preheated to +65° C., by collecting 500 µl fractions. The OD260 was read for each collected fraction, and the mRNA containing fractions were pooled and ethanol precipitated at −20° C. for 12 h. The poly(A)+ RNA was collected by centrifugation, resuspended in DEPC-DIW and stored in 5–10 µg aliquots at −80° C.

cDNA Synthesis

First Strand Synthesis

Double-stranded cDNA was synthesized from 5 µg of poly(A)+ RNA by the RNase H method (Gubler et al. (1983) Gene 25, 263–269; Sambrook et al.(1989), Molecular Cloning: A Laboratory Manual, 2 Ed., Cold Spring Harbor Laboratory, Cold Spring Harbar, N.Y.) using the hair-pin modification. The poly(A)+RNA (5 µg in 5 µl of DEPC-treated water) was heated at 70° C. for 8 min. in a pre-siliconized, RNase-free Eppendorph tube, quenched on ice, and combined in a final volume of 50 µl with reverse transcriptase buffer (50 mM Tris-Cl, pH 8.3, 75 mM KCl, 3 mM MgCl2, 10 mM DTT, Bethesda Research Laboratories) containing 1 mM of dATP, dGTP and dTTP, and 0.5 mM of 5-methyl-dCTP (Pharmacia), 40 units of human placental ribonuclease inhibitor (RNasin, Promega), 1.45 µg of oligo (dT)18- Not I primer (Pharmacia) and 1000 units of SuperScript II RNase H- reverse transcriptase (Bethesda Research Laboratories). First-strand cDNA was synthesized by incubating the reaction mixture at 45° C. for 1 h. After synthesis, the mRNA:cDNA hybrid mixture was gel filtrated through a MicroSpin S-400 HR (Pharmacia) spin column according to the manufacturer's instructions.

Second Strand Synthesis

After the gel filtration, the hybrids were diluted in 250 µl of second strand buffer (20 mM Tris-Cl, pH 7.4, 90 mM KCl, 4.6 mM MgCl2, 10 mM (NH4)2SO4, 0.16 mM βNAD+) containing 200 µM of each dNTP, 60 units of *E. coli* DNA polymerase I (Pharmacia), 5.25 units of RNase H (Promega) and 15 units of *E. coli* DNA ligase (Boehringer Mannheim). Second strand cDNA synthesis was performed by incubating the reaction tube at 16° C. for 2 h, and an additional 15 min at 25° C. The reaction was stopped by addition of EDTA to 20 mM final concentration followed by phenol and chloroform extractions.

Mung Bean Nuclease Treatment

The double-stranded (ds) cDNA was ethanol precipitated at −20° C. for 12 hours by addition of 2 vols of 96% EtOH, 0.2 vol 10 M NH4Ac, recovered by centrifugation, washed in 70% EtOH, dried (SpeedVac), and resuspended in 30 µl of Mung bean nuclease buffer (30 mM NaAc, pH 4.6, 300 mM NaCl, 1 mM ZnSO4, 0.35 mM DTT, 2% glycerol)

containing 25 units of Mung bean nuclease (Pharmacia). The single-stranded hair-pin DNA was clipped by incubating the reaction at 30° C. for 30 min, followed by addition of 70 µl 10 mM Tris-Cl, pH 7.5, 1 mM EDTA, phenol extraction, and ethanol precipitation with 2 vols of 96% EtOH and 0.1 vol 3M NaAc, pH 5.2 on ice for 30 min.

Blunt-ending With T4 DNA Polymerase

The ds cDNAs were recovered by centrifugation (20,000 rpm, 30 min.), and blunt-ended with T4 DNA polymerase in 30 µl of T4 DNA polymerase buffer (20 mM Tris-acetate, pH 7.9, 10 mM MgAc, 50 mM KAc, 1 mM DTT) containing 0.5 mM each dNTP and 5 units of T4 DNA polymerase (New England Biolabs) by incubating the reaction mixture at +16° C. for 1 hour. The reaction was stopped by addition of EDTA to 20 mM final concentration, followed by phenol and chloroform extractions and ethanol precipitation for 12 h at −20° C. by adding 2 vols of 96% EtOH and 0.1 vol of 3M NaAc, pH 5.2.

Adaptor Ligation, Not I Digestion and Size Selection

After the fill-in reaction the cDNAs were recovered by centrifugation as above, washed in 70% EtOH, and the DNA pellet was dried in SpeedVac. The cDNA pellet was resuspended in 25 µl of ligation buffer (30 mM Tris-Cl, pH 7.8, 10 µmM MgCl2, 10 mM DTT, 0.5 mM ATP) containing 2.5 µg non-palindromic BstXI adaptors (1 µg/µl, Invitrogen) and 30 units of T4 ligase (Promega) by incubating the reaction mix at +16° C. for 12 h. The reaction was stopped by heating at +65° C. for 20 min, and then on ice for 5 min. The adapted cDNA was digested with Not I restriction enzyme by addition of 20 µl autoclaved water, 5 µl of 10×Not I restriction enzyme buffer (New England Biolabs) and 50 units of Not I (New England Biolabs), followed by incubation for 2.5 hours at +37° C. The reaction was stopped by heating the sample at +65° C. for 10 min. The cDNAs were size-fractionated by agarose gel electrophoresis on a 0.8% SeaPlaque GTG low melting temperature agarose gel (FMC) in 1×TBE (in autoclaved water) to separate unligated adaptors and small cDNAs. The gel was run for 12 hours at 15 V, the cDNA was size-selected with a cut-off at 0.7 kb by cutting out the lower part of the agarose gel, and the cDNA was concentrated by running the gel backwards until it appeared as a compressed band on the gel. The cDNA (in agarose) was cut out from the gel, and the agarose was melted at 65° C. in a 2 ml Biopure Eppendorph tube (Eppendorph). The sample was treated with agarase by adding 0.1 vol of 10×agarase buffer (New England Biolabs) and 2 units per 100 µl molten agarose to the sample, followed by incubation at 45° C. for 1.5 h. The cDNA sample was phenol and chloroform extracted, and precipitated by addition of 2 vols of 96% EtOH and 0.1 vol of 3M NaAc, pH 5.2 at −20° C. for 12 h.

EXAMPLES

Example 1

Providing Novel DNA Sequences Encoding Polypeptide with Xylanase Activity

Novel sequences with xylanase activity were provided according to the method of the invention using the glycosyl hydrolase family 11 xylanase derived from Bacillus sp. (SEQ ID No 1) as the known structural gene sequence.

Identification of Conserved Regions by Alignment

An amino acid sequence alignment of ten family 11 xylanases revealed at least 3 conserved sequences. Two of these conserved sequences are used to design appropriate PCR primers for amplification of unknown DNA sequences.

The first conserved sequence shown in SEQ ID No. 3 i.e. "DGGTYDIY" corresponding to position 433–456 in SEQ ID NO 1.

The second conserved sequence shown in SEQ 4, i.e. "EGYQSSG" corresponding to position 631–651 in SEQ ID NO 1.

PCR Amplification of the Known and Unknown Partial Structural Gene Sequences

Figure 4:
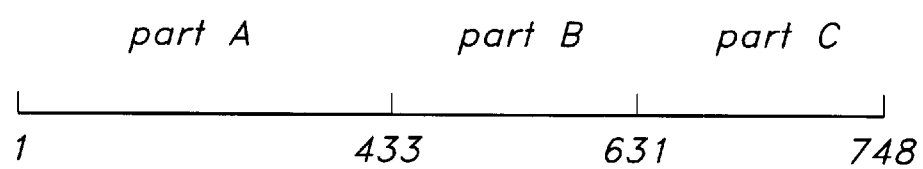
FIG. 4 shows a schematically a novel hybrid gene provided according to the invention. Part A and Part C are the known sequences linked to the unknown Part B.

Initially the N-terminal end (i.e. Part A) and the C-terminal (i.e. Part C) of the known xylanase gene, in which the unknown sequence (i.e. Part B) is to be inserted, were amplified by PCR (see FIG. 4)

Part A was PCR amplified using the two primers (i.e. primer e and primer $a_{rc}$) and as DNA template a plasmid carrying the known xylanase gene (i.e. SEQ ID NO 1).

Primer e (shown in SEQ ID NO 5 and FIG. 1) is an exact N-terminal primer extended with a sequence which included an EcoRI restriction recognition site.

Primer $a_{rc}$ (shown in SEQ ID NO 6 and FIG. 1) is a reverse and complement sequence primer of position 411–432 in SEQ ID NO 1.

Part C was PCR amplified using the two primers (i.e. primer f and primer $d_{rc}$) mentioned below and as DNA template a plasmid carrying the known xylanase gene.

Primer f is an exact reverse and complement C-terminal primer extended with a sequence which having a SalI restriction recognition site is shown in SEQ ID No. 7.

Primer $d_{rc}$ (SEQ ID No 8) was designed on the basis of position 651–672 in SEQ ID No. 1.

Part B was PCR amplified using two primers (i.e. primer ab and primer cd) and as DNA template DNA purified from a soil sample using the FastDNA® SPIN Kit.

Primer ab (SEQ ID NO 9) has the exact sequence of position 411–432 in SEQ ID 1 extended with degenerated xylanase consensus sequence covering position 433–452 in SEQ ID NO 1.

Primer cd (SEQ ID NO: 10) has the exact reverse and complement sequence of position 672–651 in SEQ ID NO 1 extended with degenerated xylanase consensus sequence covering position 650–631 in SEQ ID NO 1.

The N-terminal part of the known xylanase gene (Part A) was PCR amplified for 9 min. at 94° C. followed by 30 cycles (45 second at 94° C., 45 seconds at 50° C. and 1 min. at 72° C.) and finally for 7 min. at 72° C. This gave a PCR product of approx. 450 bp.

The C-terminal part (Part C) of the known xylanase gene was PCR amplified for 9 min. at 94° C. followed by 30 cycles (45 seconds at 94° C., 45 seconds at 50° C. and 1 min. at 72° C.) and finally for 7 min. at 72° C. This gave a PCR product of approx. 100 bp.

The unknown sequences (Part B) was PCR amplified for 9 min. at 94° C. followed by 40 cycles(45 seconds at 94° C., 45 seconds at 50° C. and 1 min. at 72° C.) and finally for 7 min. at 72° C. This gave a PCR product of approx. 260 bp.

The PCR products mentioned above were carefully purify to avoid remains of template DNA which can produce false positive bands in the following SOE-PCR where the products are joined together to form hybrid sequences.

Construction of Hybrid Sequences

Hybrid sequences containing the N- and C-terminal parts of the known xylanase gene with core part of unknown genes was constructed by splicing by overlap extension PCR (SOE-PCR).

Equal molar amounts of Part A, Part B and Part C PCR products were mixed and PCR amplified under standard conditions except that the reaction was started without any primers.

The reaction started with 9 min. at 94° C. followed by 4 cycles (45 seconds at 94° C., 45 seconds at 50° C., 1 min. at 72° C.), then primers e and f (SEQ ID No. 5 and 7, respectively) were added, followed by 25 cycles (45 seconds at 94° C., 45 seconds at 50° C., 1 min. at 72° C.) and finally 7 min. at 72° C. This gave a SOE-PCR product of the expected size of approx. 770 bp.

Cloning of the Hybrids

The SOE-PCR product was purified using the QIAquick PCR Purification Kit Protocol and digested overnight with EcoRI and SalI according to the manufacturers recommendation. The digested product was then ligated into an *E. coli* expression vector overnight at 16° C. (in this case a vector where the hybrid gene is under control of a temperature sensitive lamda repressor promoter).

The ligation mixture was transformed into electromax DH10B *E. coli* cells (GIBCO BRL) and plated on LB-ampicillin plates containing 0.1% AZCL Birch xylan. After induction of the promoter (by increasing the temperature to 42° C.) xylanase positive colonies were identified as colonies surrounded by a blue halo.

Plasmid DNA was isolated from positive *E. coli* colonies using standard procedures and sequenced with the Taq deoxy terminal cycle sequencing kit (Perkin Elmer, USA) using an Applied Biosystems 373A automated sequencer according to the manufacturers instructions.

The sequence of a positive clone is shown in SEQ ID NO 11 and the corresponding protein sequence is shown in SEQ ID NO 12.

An alignment of the known xylanase sequence (SEQ ID NO 2) and the novel DNA sequence provided according to the method of the invention can be seen in FIG. 3. As can be seen the two protein sequences differs between the two identified conserved regions (i.e. SEQ ID NO 3 and SEQ ID NO 4, respectively).

Example 2

Efficiency of the Method of the Invention

Degenerated primers were designed on the basis of conserved regions identified by alignment of a number of family 5 cellulases and family 10 and 11 xylanases found on the Internet in ExPASy under Prosite (Dictionary of protein sites and patterns).

PCR amplification of a number of unknown structural gene sequences from soil and cow rumen samples were performed with various degenerated primers covering identified conserved region sequences to show how effective the method of the invention is.

The PCR products were cloned into the vector pCR™ II, provided with the original TA cloning kit from Invitrogen. Said vector provides the possibility to make blue-white screening, the white colonies were selected and the inserts were sequenced.

When editing the Sequence Listing below all sequences outside the two EcoRI sites in the polylinker were removed. Therefore all sequences have a small additional part of the polylinker (i.e. from the EcoRI site to the TT overhang) in both ends of the sequences. These extensions are "GAAT-TCGGCT" and "AAGCCG".

1. PCR primers were designed on the basis of identified conserved regions #1 GWNLGN and #2 (E/D)HLIFE of cellulases from the glycosyl hydrolase family 5 aiming to provide novel sequences with cellulase activity.
SEQ ID No 13 and 14 show the sequences obtained from a soil sample. SEQ ID NO 15 and 16 show the sequences obtained from a cow rumen sample.

2. PCR primers were designed on the basis of identified conserved regions #1 GWNLGN and #3 RA(S/T)GGNN of cellulases from the glycosyl hydrolase family 5 aiming to provide novel sequences with cellulase activity.
SEQ ID NO 17 to 19 show the sequences obtained from a cow rumen sample.

3. PCR primers were designed on the basis of identified conserved regions #2 (E/D)HLIFE and #3 RA(S/T)GGNN of cellulases from the glycosyl hydrolase family 5 aiming to provide novel sequences with cellulase activity.
SEQ ID NO 20 to 22 show the sequences obtained from a cow rumen sample.

4. PCR primers were designed on the basis of identified conserved regions #4 HTLVWH and #5 WDVVNE of xylanases from the glycosyl hydrolase family 10 aiming to provide novel sequences with xylanase activity.
SEQ ID NO 23 to 28 show the sequences obtained from a cow rumen sample.

5. PCR primers were designed on the basis of the identified conserved regions #4 HTLVWH and #6 (F/Y) (I/Y) NDYN of xylanases from the glycosyl hydrolase family 10 aiming to provide novel sequences with xylanase activity.
SEQ ID NO 29 to 33 show the sequences obtained from a cow rumen sample.

6. PCR primers were designed on the basis of the identified conserved regions #5 WDVVNE and #6 (F/Y) (I/Y) NDYN of xylanases from the glycosyl hydrolase family 10 aiming to provide novel sequences with xylanase activity.
SEQ ID NO 34 to 36 show the sequences obtained from a soil sample. SEQ ID NO 37 to 45 show the sequences obtained from a cow rumen sample 7. PCR primers were designed on the basis of the identified conserved regions #8 DGGTYDIY and #9 EGYQSSG of xylanases from the glycosyl hydrolase family 11 aiming to provide novel sequences with xylanase activity.
SEQ ID NO 46 to 49 show the sequences obtained from a soil sample. SEQ ID NO 50 to 54 show the sequences obtained from a cow rumen sample.

60 clones with inserts were sequenced and resulted in 43 different sequences all encoding either a part of a cellulase or a part of a xylanase. Only 2 of the 43 sequences were similar to sequence found in the sequence databases Genbank.

SEQ ID NO 49 was found to be similar to Xylanase A from *Bacillus pumilus*. SEQ ID NO 42 was found to be similar to a xylanase from *Prevotella ruminicola*.

Example 3

Construction of Novel Hybrid DNA Sequences Encoding Polypeptides with Endoglucanase Activity Novel hybrid DNA sequences with endoglucanase activity were provided by first identifying two conserved regions common for the following family 45 cellulases (see WO 96/29397): *Humicola insolens* EGV (disclosed in WO 91/17243), *Fusarium oxysporum* EGV (Sheppard et al., Gene (1994), Vol. 15, pp.163–167), *Thielavia terrestris*, *Myceliophthora thermophila*, and Acremonium sp (disclosed in WO 96/29397).

The amino acid sequence alignment revealed two conserved region.

The first conserved region "Thr Arg Tyr Trp Asp Cys Cys Lys Pro/Thr" shown in SEQ ID NO 57 corresponds to position 6 to 14 of SEQ ID NO 55 showing the *Humicola insolens* EG V 43 KDa endoglucanase.

The second conserved region "Trp Arg Phe/Tyr Asp Trp Phe" shown in SEQ ID NO 58 corresponding to positions 169 to 198 of SEQ ID NO 55 showing the *Humicola insolens* EGV 43 KDa endoglucanase.

Two degenerate, deoxyinosine-containing oligonucleotide primers (sense; primer s and antisense; primer as) were constructed) for PCR amplification of unknown gene sequences. The deoxyinosines are depicted by an I in the primer sequences.

Primers s and primer as are shown in SEQ ID No. 59 and 60 respectively.

The *Humicola insolens* EG V structural gene sequence (SEQ ID NO 55) was used as the known DNA sequence. A number of fungal DNA sequences mentioned below were used as the unknown sequences.

PCR Cloning of the Family 45 Cellulase Core Region and the Linker/CBD of *Humicola Insolens* EG V.

Approximately 10 to 20 ng of double-stranded, cellulase-induced cDNA from *Humicola nigrescens*, Cylindrocarpon sp., *Fusarium anguioides, Gliocladium catenulatum,* and *Trichothecium roseum* prepared, as described above in the Material and Methods section were, PCR amplified in Expand buffer (Boehringer Mannheim, Germany) containing 200 μM each dNTP and 200 pmol of each degenerate Primer s (SEQ ID NO 59) and Primer as (SEQ ID NO 60) a DNA thermal cycler (Perkin-Elmer, Cetus, USA) and 2.6 units of Expand High Fidelity polymerase (Boehringer Mannheim, Germany). 30 cycles of PCR were performed using a cycle profile of denaturation at 94° C. for 1 min, annealing at 55° C. for 2 min, and extension at 72° C. for 3 min, followed by extension at 72° C. for 5 min.

The PCR fragment coding for the linker/CBD of *H. insolens* EGV was generated in Expand buffer (Boehringer Mannheim, Germany) containing 200 μM each dNTP using 100 ng of the pCaHj418 template, 200 pmol forward primer 1 (SEQ ID NO 61), 200 pmol reverse primer 1 (SEQ ID NO 62). 30 cycles of PCR were performed as above.

Construction of Hybrid Genes Using Splicing by Overlap Extension (SOE)

The PCR products were electrophoresed in 0.7% agarose gels (SeaKem, FMC), the fragments of interest were excised from the gel and recovered by Qiagen gel extraction kit (Qiagen, USA) according to the manufacturer's instructions. The recombinant hybrid genes were generated by combining the overlapping PCR fragments from above (ca. 50 ng of each template) in Expand buffer (Boehringer Mannheim, Germany) containing 200 μM each dNTP in the SOE reaction. Two cycles of PCR were performed using a cycle profile of denaturation at 94° C. for 1 min, annealing at 50° C. for 2 min, and extension at 72° C. for 3 min, the reaction was stopped, 250 pmol of each end-primer: forward primer 2 (SEQ ID NO 63) encoding the TAKA-amylase signal sequence from *A. oryzae*, reverse primer 2 (SEQ ID NO 64) was added to the reaction mixture, and an additional 30 cycles of PCR were performed using a cycle profile of denaturation at 94° C. for 1 min, annealing at 55° C. for 2 min, and extension at 72° C. for 3 min.

Construction of the Expression Cassettes and Heterologous Expression in *Aspergillus oryzae*

The PCR-generated, recombinant fragments were electrophoresed in 0.7% agarose gels (SeaKem, FMC), the fragments were excised from the gel and recovered by Qiagen gel extraction kit (Qiagen, USA) according to the manufacturer's instructions. The DNA fragments were digested to completion with BamHI and XbaI, and ligated into BamHI/XbaI-cleaved pHD414 vector. Co-transformation of *A. oryzae* was carried out as described in Christensen et al. (1988), Bio/Technology 6, 1419–1422. The AmdS+ transformants were screened for cellulase activity using 0.1% AZCl-HE-cellulose in a plate assay as described above. The cellulase-producing transformants were purified twice through conidial spores, cultivated in 250 ml shake flasks, and the amount of secreted cellulase was estimated by SDS-PAGE, Western blot analysis and the activity assay as described earlier (Kauppinen et al. (1995), J. Biol. Chem. 270, 27172–27178;; Kofod et al. (1994), J. Biol. Chem. 269, 29182–29189; Christgau et. al, (1994), Biochem. Mol. Biol. Int. 33, 917–925).

Nucleotide Sequence Analysis

The nucleotide sequences of the novel hybrid gene fusions were determined from both strands by the dideoxy chain-termination method (Sanger et al., (1977), Proc. Natl. Acad. Sci. U.S.A. 74, 5463–5467), using 500 ng template, the Taq deoxy-terminal cycle sequencing kit (Perkin-Elmer, USA), fluorescent labeled terminators and 5 pmol of synthetic oligonucleotide primers. Analysis of the sequence data was performed according to Devereux et al., 1984 (Devereux et al., (1984), Nucleic Acids Res. 12, 387–395).

The provided novel hybrid DNS sequences an the deduced protein sequences are shown in SEQ ID No 65 to 74.

SEQ ID NO 65 shows the hybrid gene construct comprising the family 45 cellulase core region from *Humicola nigrescens* and the linker/CBD of *Humicola insolens* EG V. SEQ. ID No 66 shows the deduced amino acid sequence of the hybrid gene construct.

SEQ ID NO 67 shows the hybrid gene construct comprising the family 45 cellulase core region from Cylindrocarpon sp. and the linker/CBD of *Humicola insolens* EG V. SEQ ID NO 68 shown the deduced amino acid sequence of the hybrid gene construct.

SEQ ID NO shows the hybrid gene construct comprising the family 45 cellulase core region from *Fusarium anguioides* and the linker/CBD of *Humicola insolens* EG V. SEQ ID NO 70 shows the deduced amino acid sequence of the hybrid gene construct.

SEQ ID NO 71 shows the hybrid gene construct comprising the family 45 cellulase core region from *Gliocladium catenulatum* and the linker/CBD of *Humicola insolens* EG V. SEQ ID NO 72 shows the deduced amino acid sequence of the hybrid gene construct.

SEQ ID NO 73 shows the novel gene construct comprising the family 45 cellulase core region from *Trichothecium roseum* and the linker/CBD of *Humicola insolens* EG V. SEQ ID NO 74 shows the deduced amino acid sequence of the hybrid gene construct.

What is claimed is:

1. A method for providing a hybrid polypeptide having an activity of interest, comprising:
   i) performing PCR amplification using an uncharacterized DNA sample and oligonucleotide primers with homology to one or more known genes encoding a polypeptide exhibiting the activity of interest, to obtain one or more PCR products of unknown sequence;
   ii) linking the obtained PCR products of unknown sequence to a 5' structural gene sequence and a 3' structural gene sequence, wherein the 5' and 3' structural gene sequences are derived from one or more genes encoding a polypeptide exhibiting the activity of interest, to form hybrid DNA sequences;
   iii) expressing the hybrid DNA sequences; and
   iv) screening the expressed hybrid DNA sequences to identify a sequence encoding a polypeptide exhibiting the activity of interest or a related activity.

2. The method of claim 1, wherein the primers in step i) have homology to conserved regions in one or more known structural genes or encode peptides or polypeptides having homology to known structural genes.

3. The method of claim 2, wherein the PCR primers in step i) are degenerate.

4. The method of claim 1, wherein the uncharacterized DNA sample is naturally occurring DNA.

5. The method of claim 1, wherein the uncharacterized DNA sample is derived from a microorganism which has not been subjected to in vitro selection.

6. The method of claim 1, wherein the uncharacterized DNA sample is derived from a non-isolated microorganism.

7. The method of claim 1, wherein the 5' structural gene sequence and the 3' structural gene sequence originate from two different structural genes encoding polypeptides having the same activity.

8. The method of claim 1, wherein the 5' structural gene sequence and the 3' structural gene sequence originate from the same structural gene sequence.

9. The method of claim 1, wherein the 5' structural gene sequence and the 3' structural gene sequence originate from two different structural gene sequences encoding polypeptides having different activities.

10. A method for providing a hybrid polypeptide exhibiting an activity of interest, comprising:
    i) performing PCR amplification using a DNA sample derived from one or more microorganisms and PCR primers homologous to conserved regions of a known gene encoding a polypeptide exhibiting the activity of interest to obtain one or more PCR products of unknown sequence;
    ii) inserting the obtained one or more PCR products of unknown sequence into a gene encoding a parent polypeptide having the activity of interest, wherein the gene is situated in an expression vector, wherein a library or expression vectors containing hybrid DNA sequences is provided;
    iii) transforming the expression vector library into a suitable host cell to obtain a library of transformed clones;
    iv) culturing the library of step iii) under suitable conditions for expression of said hybrid polypeptides; and
    v) screening the library of hybrid polypeptides to identify a polypeptide exhibiting the activity of interest or related activity.

11. The method of claim 10, wherein the DNA sample is derived from a prokaryotic or eukaryotic microorganism.

12. The method of claim 1, wherein the DNA sample is derived form a non-cultivable organism.

13. The method of claim 12, wherein the non-cultivable organism is selected from the group consisting of algae, fungi, and protozoa.

14. The method of claim 13, wherein the non-cultivable organism is selected from the group consisting of extremophiles and plantonic marine organisms.

15. The method of claim 10, wherein the DNA sample is derived from a cultivable organism.

16. The method of claim 15, wherein the cultivable organism is selected from the group consisting of bacteria, filamentous fungi, and yeasts.

17. The method of claim 16, wherein the DNA sample comprises a plasmid.

18. The method of claim 10, wherein the activity of interest is an enzymatic activity.

19. The method of claim 18, wherein the enzymatic activity is selected from the group consisting of phosphatases, oxidoreductases, transferases, and hydrolases.

20. The method of claim 10, wherein the host cell is a microorganism selected from the group consisting of yeast and bacteria.

21. The method of claim 20, wherein the host cell is *Saccharomyces cerevisiae*.

22. The method of claim 20, wherein the host cell is a bacterium selected from the group consisting of Bacillus sp and *Escherchia coli*.

23. The method of claim 1, wherein the activity of interest is an enzymatic activity.

24. The method of claim 23, wherein the enzymatic activity is assayed by wash performance.

25. The method of claim 1, further comprising isolating the hybrid polypeptide exhibiting the activity of interest identified in step iv).

26. The method of claim 25, further comprising sequencing the hybrid DNA sequence encoding the identified hybrid pglypeptide of step iv).

27. The method of claim 1, wherein the hybrid polypeptide identified in step (iv) exhibits an altered activity relative to the activity of the polypeptide encoded by said 5' and 3' structural gene sequences.

28. The method of claim 10, further comprising isolating the hybrid DNA sequence encoding the hybrid polypepide exhibiting the activity of interest identified in step v).

29. The method of claim 10, further comprising determining the sequence of the inserted PCR product.

30. The method of claim 10, wherein the gene into which the PCR product is inserted is not identical to the gene from which the PCR product is obtained.

31. The method of claim 10, wherein the hybrid polypeptide identified in step (v) exhibits an altered activity relative to the activity of the parent polypeptide.

32. A method of providing a hybrid polypeptide exhibiting an activity of interest, comprising:
- i) performing PCR amplification using a DNA sample derived from one or more microorganisms using a first primer and a second primer to provide a PCR fragment of an unknown gene having the activity of interest to obtain one or more PCR products of unknown sequence; wherein the first primer has an exact sequence matching a sequence at the 5' end of a known gene encoding a polypeptide having the activity of interest and a degenerated consensus sequence; wherein the second primer has an exact sequence matching a sequence at the 3' end of a known gene encoding a polypeptide having the activity of interest and a degenerated consensus sequence;
- ii) inserting the obtained one or more PCR products of unknown sequence into a gene encoding a parent polypeptide having the activity of interest, wherein the gene is situated in an expression vector, wherein a library or expression vectors containing hybrid DNA sequences is provided;
- iii) transforming the expression vector library into a suitable host cell to obtain a library of transformed clones;
- iv) culturing the library of step iii) under suitable conditions for expression of said hybrid polypeptides; and
- v) screening the library of hybrid polypeptides to identify a polypeptide exhibiting the activity of interest or related activity.

33. The method of claim 32, wherein the first PCR primer comprises an exact sequence of the 5' end of a known gene encoding a polypeptide having the activity of interest and a sequence comprising a restriction site corresponding to a restriction site in the expression vector; and wherein the second PCR primer comprises an exact sequence of the 3' end of a known gene encoding a polypeptide having the activity of interest and a sequence comprising a restriction site corresponding to a restriction site in the expression vector.

* * * * *

SEQUENCE LISTING

```
<160> NUMBER OF SEQ ID NOS: 74

<210> SEQ ID NO 1
<211> LENGTH: 744
<212> TYPE: DNA
<213> ORGANISM: Bacillus
<220> FEATURE:
<221> NAME/KEY: CDS
<222> LOCATION: (1)...(744)
```

<400> SEQUENCE: 1

```
atg aga caa aag aaa ttg acg ttc att tta gcc ttt tta gtt tgt ttt      48
Met Arg Gln Lys Lys Leu Thr Phe Ile Leu Ala Phe Leu Val Cys Phe
 1               5                  10                  15 gca cta acc tta cct gca gaa ata att cag gca caa atc gtc acc gac      96
Ala Leu Thr Leu Pro Ala Glu Ile Ile Gln Ala Gln Ile Val Thr Asp
                 20                  25                  30 aat tcc att ggc aac cac gat ggc tat gat tat gaa ttt tgg aaa gat     144
Asn Ser Ile Gly Asn His Asp Gly Tyr Asp Tyr Glu Phe Trp Lys Asp
             35                  40                  45 agc ggt ggc tct ggg aca atg att ctc aat cat ggc ggt acg ttc agt     192
Ser Gly Gly Ser Gly Thr Met Ile Leu Asn His Gly Gly Thr Phe Ser
 50                  55                  60 gcc caa tgg aac aat gtt aac aac ata tta ttc cgt aaa ggt aaa aaa     240
Ala Gln Trp Asn Asn Val Asn Asn Ile Leu Phe Arg Lys Gly Lys Lys
 65                  70                  75                  80 ttc aat gaa aca caa aca cac caa caa gtt ggt aac atg tcc ata aac     288
Phe Asn Glu Thr Gln Thr His Gln Gln Val Gly Asn Met Ser Ile Asn
                 85                  90                  95 tat ggc gca aac ttc cag cca aac gga aat gcg tat tta tgc gtc tat     336
Tyr Gly Ala Asn Phe Gln Pro Asn Gly Asn Ala Tyr Leu Cys Val Tyr
                100                 105                 110 ggt tgg act gtt gac cct ctt gtc gaa tat tat att gtc gat agt tgg     384
Gly Trp Thr Val Asp Pro Leu Val Glu Tyr Tyr Ile Val Asp Ser Trp
            115                 120                 125 ggc aac tgg cgt cca cca ggg gca acg cct aag gga acc atc act gtt     432
Gly Asn Trp Arg Pro Pro Gly Ala Thr Pro Lys Gly Thr Ile Thr Val
130                 135                 140 gat gga gga aca tat gat atc tat gaa act ctt aga gtc aat cag ccc     480
Asp Gly Gly Thr Tyr Asp Ile Tyr Glu Thr Leu Arg Val Asn Gln Pro
145                 150                 155                 160 tcc att aag ggg att gcc aca ttt aaa caa tat tgg agt gtc cga aga     528
Ser Ile Lys Gly Ile Ala Thr Phe Lys Gln Tyr Trp Ser Val Arg Arg
                165                 170                 175 tcg aaa cgc acg agt ggc aca att tct gtc agc aac cac ttt aga gcg     576
Ser Lys Arg Thr Ser Gly Thr Ile Ser Val Ser Asn His Phe Arg Ala
                180                 185                 190 tgg gaa aac tta ggg atg aac atg ggg aaa atg tat gaa gtc gcg ctt     624
Trp Glu Asn Leu Gly Met Asn Met Gly Lys Met Tyr Glu Val Ala Leu
            195                 200                 205 act gta gaa ggc tat caa agt agc gga agt gct aat gta tat agc aat     672
Thr Val Glu Gly Tyr Gln Ser Ser Gly Ser Ala Asn Val Tyr Ser Asn
        210                 215                 220 aca cta aga att aac ggt aac cct ctc tca act att agt aat gac aag     720
Thr Leu Arg Ile Asn Gly Asn Pro Leu Ser Thr Ile Ser Asn Asp Lys
225                 230                 235                 240 agc ata act cta gat aaa aac aat                                     744
Ser Ile Thr Leu Asp Lys Asn Asn
                245

<210> SEQ ID NO 2
<211> LENGTH: 248
<212> TYPE: PRT
<213> ORGANISM: Bacillus

<400> SEQUENCE: 2

Met Arg Gln Lys Lys Leu Thr Phe Ile Leu Ala Phe Leu Val Cys Phe
 1               5                  10                  15

Ala Leu Thr Leu Pro Ala Glu Ile Ile Gln Ala Gln Ile Val Thr Asp
```

```
            20                  25                  30
Asn Ser Ile Gly Asn His Asp Gly Tyr Asp Tyr Glu Phe Trp Lys Asp
                 35                  40                  45

Ser Gly Gly Ser Gly Thr Met Ile Leu Asn His Gly Gly Thr Phe Ser
     50                  55                  60

Ala Gln Trp Asn Asn Val Asn Asn Ile Leu Phe Arg Lys Gly Lys Lys
 65                  70                  75                  80

Phe Asn Glu Thr Gln Thr His Gln Gln Val Gly Asn Met Ser Ile Asn
                 85                  90                  95

Tyr Gly Ala Asn Phe Gln Pro Asn Gly Asn Ala Tyr Leu Cys Val Tyr
                100                 105                 110

Gly Trp Thr Val Asp Pro Leu Val Glu Tyr Tyr Ile Val Asp Ser Trp
                115                 120                 125

Gly Asn Trp Arg Pro Pro Gly Ala Thr Pro Lys Gly Thr Ile Thr Val
            130                 135                 140

Asp Gly Gly Thr Tyr Asp Ile Tyr Glu Thr Leu Arg Val Asn Gln Pro
145                 150                 155                 160

Ser Ile Lys Gly Ile Ala Thr Phe Lys Gln Tyr Trp Ser Val Arg Arg
                165                 170                 175

Ser Lys Arg Thr Ser Gly Thr Ile Ser Val Ser Asn His Phe Arg Ala
                180                 185                 190

Trp Glu Asn Leu Gly Met Asn Met Gly Lys Met Tyr Glu Val Ala Leu
                195                 200                 205

Thr Val Glu Gly Tyr Gln Ser Ser Gly Ser Ala Asn Val Tyr Ser Asn
            210                 215                 220

Thr Leu Arg Ile Asn Gly Asn Pro Leu Ser Thr Ile Ser Asn Asp Lys
225                 230                 235                 240

Ser Ile Thr Leu Asp Lys Asn Asn
                245

<210> SEQ ID NO 3
<211> LENGTH: 8
<212> TYPE: PRT
<213> ORGANISM: Prokaryotic

<400> SEQUENCE: 3

Asp Gly Gly Thr Tyr Asp Ile Tyr
 1               5

<210> SEQ ID NO 4
<211> LENGTH: 7
<212> TYPE: PRT
<213> ORGANISM: Prokaryotic

<400> SEQUENCE: 4

Glu Gly Tyr Gln Ser Ser Gly
 1               5

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
gcgaattcat gagacaaaag aaattgacg                                29
```

```
<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
aacagtgatg gttcccttag gc                                              22

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
ctagagtcga cttaattgtt tttatctaga g                                    31

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
aacagtgatg gttcccttag gc                                              22

<210> SEQ ID NO 9
<211> LENGTH: 42
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(42)
<223> OTHER INFORMATION: n = a, c, g, or t

<400> SEQUENCE: 9
gcctaaggga accatcactg ttgayggngg nacntaygay at                        42

<210> SEQ ID NO 10
<211> LENGTH: 42
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(42)
<223> OTHER INFORMATION: n = a, c, g, or t

<400> SEQUENCE: 10
aatgctatat acattagcac ttccnswnsw ytggtanccy tc                        42

<210> SEQ ID NO 11
<211> LENGTH: 744
<212> TYPE: DNA
<213> ORGANISM: Hybrid
<220> FEATURE:
<221> NAME/KEY: CDS
<222> LOCATION: (1)...(744)

<400> SEQUENCE: 11 atg aga caa aag aaa ttg acg ttc att tta gcc ttt tta gtt tgt ttt      48
Met Arg Gln Lys Lys Leu Thr Phe Ile Leu Ala Phe Leu Val Cys Phe
 1               5                  10                  15
```

```
gca cta acc tta cct gca gaa ata att cag gca caa atc gtc acc gac      96
Ala Leu Thr Leu Pro Ala Glu Ile Ile Gln Ala Gln Ile Val Thr Asp
             20                  25                  30 aat tcc att ggc aac cac gat ggc tat gat tat gaa ttt tgg aaa gat     144
Asn Ser Ile Gly Asn His Asp Gly Tyr Asp Tyr Glu Phe Trp Lys Asp
         35                  40                  45 agc ggt ggc tct ggg aca atg att ctc aat cat ggc ggt acg ttc agt     192
Ser Gly Gly Ser Gly Thr Met Ile Leu Asn His Gly Gly Thr Phe Ser
     50                  55                  60 gcc caa tgg aac aat gtt aac aac ata tta ttc cgt aaa ggt aaa aaa     240
Ala Gln Trp Asn Asn Val Asn Asn Ile Leu Phe Arg Lys Gly Lys Lys
 65                  70                  75                  80 ttc aat gaa aca caa aca cac caa caa gtt ggt aac atg tcc ata aac     288
Phe Asn Glu Thr Gln Thr His Gln Gln Val Gly Asn Met Ser Ile Asn
                 85                  90                  95 tat ggc gca aac ttc cag cca aac gga aat gcg tat tta tgc gtc tat     336
Tyr Gly Ala Asn Phe Gln Pro Asn Gly Asn Ala Tyr Leu Cys Val Tyr
            100                 105                 110 ggt tgg act gtt gac cct ctt gtc gaa tat tat att gtc gat agt tgg     384
Gly Trp Thr Val Asp Pro Leu Val Glu Tyr Tyr Ile Val Asp Ser Trp
        115                 120                 125 ggc aac tgg cgt cca cca ggg gca acg cct aag gga acc atc act gtt     432
Gly Asn Trp Arg Pro Pro Gly Ala Thr Pro Lys Gly Thr Ile Thr Val
    130                 135                 140 gac ggg ggg acg tat gat atc tac aag cac caa cag gtc aat cag cca     480
Asp Gly Gly Thr Tyr Asp Ile Tyr Lys His Gln Gln Val Asn Gln Pro
145                 150                 155                 160 tct att cag ggc acc gcc acc ttc aat cag tac tgg tcg att cga cag     528
Ser Ile Gln Gly Thr Ala Thr Phe Asn Gln Tyr Trp Ser Ile Arg Gln
                165                 170                 175 agc aag cgg acc agc ggc act gtc act acg gca aac cac ttt aat gcc     576
Ser Lys Arg Thr Ser Gly Thr Val Thr Thr Ala Asn His Phe Asn Ala
            180                 185                 190 tgg gct gct ctt ggc atg aat atg ggt gca ttc aat tac cag atc ctc     624
Trp Ala Ala Leu Gly Met Asn Met Gly Ala Phe Asn Tyr Gln Ile Leu
        195                 200                 205 gtt act gag ggc tac caa tct acc gga agt gct aat gta tat agc aat     672
Val Thr Glu Gly Tyr Gln Ser Thr Gly Ser Ala Asn Val Tyr Ser Asn
    210                 215                 220 aca cta aga att aac ggt aac cct ctc tca act att agt aat gac aag     720
Thr Leu Arg Ile Asn Gly Asn Pro Leu Ser Thr Ile Ser Asn Asp Lys
225                 230                 235                 240 agc ata act cta gat aaa aac aat                                     744
Ser Ile Thr Leu Asp Lys Asn Asn
                245

<210> SEQ ID NO 12
<211> LENGTH: 248
<212> TYPE: PRT
<213> ORGANISM: Hybrid

<400> SEQUENCE: 12

Met Arg Gln Lys Lys Leu Thr Phe Ile Leu Ala Phe Leu Val Cys Phe
 1               5                  10                  15

Ala Leu Thr Leu Pro Ala Glu Ile Ile Gln Ala Gln Ile Val Thr Asp
             20                  25                  30

Asn Ser Ile Gly Asn His Asp Gly Tyr Asp Tyr Glu Phe Trp Lys Asp
         35                  40                  45

Ser Gly Gly Ser Gly Thr Met Ile Leu Asn His Gly Gly Thr Phe Ser
```

```
                  50                  55                  60
Ala Gln Trp Asn Asn Val Asn Asn Ile Leu Phe Arg Lys Gly Lys Lys
 65                  70                  75                  80

Phe Asn Glu Thr Gln Thr His Gln Gln Val Gly Asn Met Ser Ile Asn
                 85                  90                  95

Tyr Gly Ala Asn Phe Gln Pro Asn Gly Asn Ala Tyr Leu Cys Val Tyr
                100                 105                 110

Gly Trp Thr Val Asp Pro Leu Val Glu Tyr Tyr Ile Val Asp Ser Trp
            115                 120                 125

Gly Asn Trp Arg Pro Pro Gly Ala Thr Pro Lys Gly Thr Ile Thr Val
130                 135                 140

Asp Gly Gly Thr Tyr Asp Ile Tyr Lys His Gln Gln Val Asn Gln Pro
145                 150                 155                 160

Ser Ile Gln Gly Thr Ala Thr Phe Asn Gln Tyr Trp Ser Ile Arg Gln
                165                 170                 175

Ser Lys Arg Thr Ser Gly Thr Val Thr Thr Ala Asn His Phe Asn Ala
                180                 185                 190

Trp Ala Ala Leu Gly Met Asn Met Gly Ala Phe Asn Tyr Gln Ile Leu
            195                 200                 205

Val Thr Glu Gly Tyr Gln Ser Thr Gly Ser Ala Asn Val Tyr Ser Asn
210                 215                 220

Thr Leu Arg Ile Asn Gly Asn Pro Leu Ser Thr Ile Ser Asn Asp Lys
225                 230                 235                 240

Ser Ile Thr Leu Asp Lys Asn Asn
                245

<210> SEQ ID NO 13
<211> LENGTH: 409
<212> TYPE: DNA
<213> ORGANISM: Hybrid

<400> SEQUENCE: 13
gaattcggct tgggtggaat ctggggaaca cgttggatgc taccggagac tggatcaaag      60
ggccgtccgt gagcgcctac gagaccgcct ggggcaatcc cgtcaccacc aaggctatgt     120
tcgacggcat caaagcgtcc ggcttcaact tgttcgcat tcccgtggcg tggtccaaca      180
tgatgggccc ggactatacc attaacccgg cgttgatggc gagagtcgag aagtggtgaa     240
ttacggtctg gccgacaaca tgtatgtcat gatcaacatc cactgggacg cggctggatc     300
actaaattcc caccaactac gacgaaagca tgaagaagta taaggcggtc tggagccaga     360
tcgccgacca tttcaaagct actccgacca cctcatcttc gaaaagccg                 409

<210> SEQ ID NO 14
<211> LENGTH: 408
<212> TYPE: DNA
<213> ORGANISM: Hybrid

<400> SEQUENCE: 14
aattcggctt gggtggaatc tggggaacac tctggaagcc tgcggcggga tcaaatgcag      60
ttccgtgcgc gatttcgaga cggcttgggg caacccgtc acgaccaagg ccatgatcga     120
cggcgtcaag gcgccggct tcaggtccat acgcatcccc gtcgcctggt cgaacctgat      180
gggacctaag cccgactaca ctatcaataa gaagctgatg gcacgagtcg agcaggtcgc     240
ccggtacggc ctcgacaacg acatgtacgt catcatcaac attcactggg acgcggctgg     300
atccaccgct tctccaccga ctacaacgaa atgcatgarg aattacaagg cggtgtgggg     360
```
ccaggtagcc gaccatttca agggctactc cgaccacctc atcttcga        408

<210> SEQ ID NO 15
<211> LENGTH: 415
<212> TYPE: DNA
<213> ORGANISM: Hybrid

<400> SEQUENCE: 15
aattcggctt ctcgaagatg aggtggtcgg agtagccttt gaaatggtcg gcgatctggc      60
tccagaccgc cttatacttc ttcatgcttt cgtcgtagtt ggtggggaat ttagtgatcc     120
agccgccgtc ccagtggatg ttgatcatga catacatgtt gtcggccaga ccgtaattca     180
ccacttcctc gactctcgcc atcaacgccg gttaatggt atagtccggg cccatcatgt      240
tggaccacgc cacgggaatg cgaacaaagt tgaagccgga cgctttgatg ccgtcgaaca     300
tagccttggt ggtgacggga ttgccccagg cggtctcgta ggcgctcacg gacggcccttt   360
gatccagtct ccggtagcat ccaacgtgtt ccccarattc cacccaagcc gaatt         415

<210> SEQ ID NO 16
<211> LENGTH: 490
<212> TYPE: DNA
<213> ORGANISM: Hybrid
<220> FEATURE:
<221> NAME/KEY: misc_feature
<222> LOCATION: (1)...(490)
<223> OTHER INFORMATION: n = a, c, g, or t

<400> SEQUENCE: 16
aattcggctt gttccgcaag cgtcaaaggg gatgtgatgt accagatcaa ggcaaagctc      60
ggtctgaaat aaaactagtc aaaactagcc aaaactagtc aggctagtca gaaccagtta    120
gcacaatcgt aaaaactaaa agtatgagcg acggcaattt caaccgcgcc ctcctgccga    180
agaacgaact ctctgcagga ctcagggctg gcaaagcaca gatgcgcacc aaggctgaaa    240
caggcgttgg agactgtact cgacnaatac ttcccctctg ccgacatgtc gctccgaaac    300
gcaatccacg aacgatcctc caactcttac aacagtagga caaaggtgaa acgtatttaa    360
ttatgcttcc tgaattntca ttaacacnat gcctgtgtgg cacccatccg cgtnttcaat    420
ggtgttcacc agggcatcct ttactcatcc cacaggttaa gcaantggcc aaanaacacc    480
gtccggcttc                                                           490

<210> SEQ ID NO 17
<211> LENGTH: 491
<212> TYPE: DNA
<213> ORGANISM: Hybrid

<400> SEQUENCE: 17
aattcggctt gttgttgccg ccggtggtgc ggaccacgtc aataaaagtc tggttgtaag      60
aattctgcac agccagattc tcaggctcgg gcttgcccca gttatcgcgc aggtgaacct    120
cgttagtacc agcaaaggct acgcggtagt cgtagttggc aaactcgctg gcgatattca    180
gccacagcag ggcgagtttc tggttgttct cgtccttgta ctgataggta ggacraccct    240
ccagccactt gtcgtgatgc gtattgatga tgactttag gtcattctcg aagcaccarc     300
ccacaacctc tttgatacgt gccagccaag ccttgtcaat gctcatggca acgggattgg    360
tgatgttgca ctgccaccgg amsggaatgc ggatggcgtt raaactgcat ccttgactgc    420
cttgataact ttttttgttac aacgggattg ccccatgccg tctcacccttt aatactgttc   480

```
<210> SEQ ID NO 18
<211> LENGTH: 574
<212> TYPE: DNA
<213> ORGANISM: Hybrid
<220> FEATURE:
<221> NAME/KEY: misc_feature
<222> LOCATION: (1)...(574)
<223> OTHER INFORMATION: n = a, c, g, or t

<400> SEQUENCE: 18
aattcggctt gttgttgccg ccggtggtac ggatggtgtt caccaccaac tggttccact    60
cgttgagggt tttatactgc ttaccgccat cggtacggtt tgcgccccat ccccagccgc   120
cgtcctgaat ctcgttgaac gactcgaata tgaggaattc gcccttgtcc ttgaaggctt   180
cggcaatctg tttccangtt ttctcaatac ggttcttgat gttgctgttg gtcgttgaat   240
tgttggcagc gcccttaatg tcaaccagta ctcatcgtga tgcatgttca ggatnacntt   300
cagtccggca cttcggccca ctccacattc tgcctgactt ctgctatgta tttagcatct   360
atccccattc caaatgtttc tggtanttgc ccatgttacc cganacttan gtgctggcac   420
aacgttttta ngtttgttaa aaaccgcaaa ggcttggcat ttccaatatc ccantgggga   480
accnaacntc ncaccngcc ggtacaaatg gtncccccntt tcccccaacc caaatccncc   540
ncnggggcc gttacnattg natcnaaccg gtac                                574

<210> SEQ ID NO 19
<211> LENGTH: 520
<212> TYPE: DNA
<213> ORGANISM: Hybrid
<220> FEATURE:
<221> NAME/KEY: misc_feature
<222> LOCATION: (1)...(520)
<223> OTHER INFORMATION: n = a, c, g, or t

<400> SEQUENCE: 19
aattcggctt gttgttgccg ccggtggttc tcacggtggt gacgaagctc tgagcatanc    60
tgttgatggc gttgtaggcc gatgtggcta tggcttcgtt gtacctgccg gtagcggcaa   120
aggatgcgaa acaccaggag ctcaagggat ccagcatctc gttgaagctc tcgaagagca   180
agcgctgtcc gcagtcccgg aattcctgtg ctatctgctg ccacagacgt tcatancggg   240
agcggttcan cgcgtatttg tcctcggang ccttgatcca cnacttgaaa cnanttgctg   300
tctgcgcccg tgtcgtggtg aacgttgaat natgcagtac aagccctggt ctagganact   360
atcaccactt catgcacgcg ggccatccac gccncatcca cnttgccggc gctgtccatn   420
ttgttatacc acttcatggc ccacggatgg caccaaaccc ggatctttnt cntcctgaan   480
aacaangggt ggtgggatat taacccaaca ggtccgaaga                         520

<210> SEQ ID NO 20
<211> LENGTH: 193
<212> TYPE: DNA
<213> ORGANISM: Hybrid

<400> SEQUENCE: 20
aattcggctt gagcacctga tttttgaggg ctacaacgag atgctcgaca agtatgactc    60
ctggtgtttt gccaccttcg gacgctcggc aggctataac gctacagacg ccgccgatgc   120
ctataaagcc atcaacaact atgccagag cttcgtcaac gccgtacgca ccaccggcgg   180
caacaacaag ccg                                                     193
```

<210> SEQ ID NO 21
<211> LENGTH: 160
<212> TYPE: DNA
<213> ORGANISM: Hybrid

<400> SEQUENCE: 21
aattcggctt gagcacttga ttttcgaggc ctacaacgag atgctcgatg cccagagctc     60
gtggaacttt gcccagacca gcacagccta tgatgctatc aacaactatg cccaaagctt    120
cgtcaacatt gttcgtacca gcggcggcaa caacaagccg                          160

<210> SEQ ID NO 22
<211> LENGTH: 193
<212> TYPE: DNA
<213> ORGANISM: Hybrid

<400> SEQUENCE: 22
aattcggctt gagcatttga tcttcgagag ttacaacgag atgctcgata cggaagattc     60
ctggtgcttc gcctcgtttg cagcgcaggg cagttacaat gccaccatcg cgcgttcggc    120
ctacaacggc attaatagct atgcgcagac tttcgtcaac accgtacgta ccaccggcgg    180
caacaacaag ccg                                                       193

<210> SEQ ID NO 23
<211> LENGTH: 166
<212> TYPE: DNA
<213> ORGANISM: Hybrid

<400> SEQUENCE: 23
aattcggctt cayacgctgg tgtggcactc tcagatcggt cgttggatga ctgccgaggg     60
tacaaccaag gagcagttct atgctcgtat gaagaaccat atccaggcta tcgttactcg    120
ttacaaggat gtggtgtact gctgggacgt cgtcaacgag aagccg                   166

<210> SEQ ID NO 24
<211> LENGTH: 178
<212> TYPE: DNA
<213> ORGANISM: Hybrid

<400> SEQUENCE: 24
aattcggctt ctcgttaacg acgtcccagg catcgatctt accgcagaaa tggccggcta     60
ccgtctctat gtaactgcgc atggtctcaa ccatctcatc gtggctcttg ggagtgccgt    120
cagcgtggtt gaaaagaaa tcgggagtct gattgtgcca caccagcgta tgaagccg      178

<210> SEQ ID NO 25
<211> LENGTH: 181
<212> TYPE: DNA
<213> ORGANISM: Hybrid

<400> SEQUENCE: 25
aattcggctt cayacgctgg tgtggcactc gcaggcaccc gactggtggt ttaccaacgg     60
ctatgctgcc agccctgtct caaaggaagt gctgaaagag cggctcatca agcatattaa    120
gaccgttgtt ggccatttca agggccaagt ctttggctgg acgtcgtca acgaraagcc    180 g                                                                    181

<210> SEQ ID NO 26
<211> LENGTH: 199
<212> TYPE: DNA

<210> SEQ ID NO 26
<400> SEQUENCE: 26

```
aattcggctt catacgttgg tgtggcacaa tcagacgccg gcctggttct tccgcagggg    60
ctacaacgag aacctgcctc tggcggaccg cgagaccatg ctggcgaggc tggagagcta   120
tatccgcggt gtgctgacct atgtgcagga gaattatccc gggatcgtct acgcctggga   180
cgtcgtcaac gagaagccg                                                199
```

<210> SEQ ID NO 27
<211> LENGTH: 185
<212> TYPE: DNA
<213> ORGANISM: Hybrid
<220> FEATURE:
<221> NAME/KEY: misc_feature
<222> LOCATION: (1)...(185)
<223> OTHER INFORMATION: n = a, c, g, or t

<400> SEQUENCE: 27

```
aattcggctt ggcacggaca gacgccgcag tggttcttct acgagaacta taatacttca    60
ggaaaacttg caagcaggga aacgatgctg gcaagaatgg gaaactatat taaggcgtg    120
cttggcttcg tgcaggacaa ttatcccggc gtcatctatg cgtgggacgt tgtcaacgag   180
aaccg                                                               185
```

<210> SEQ ID NO 28
<211> LENGTH: 208
<212> TYPE: DNA
<213> ORGANISM: Hybrid

<400> SEQUENCE: 28

```
atctgcagaa attcggcttc tcgttaacga cgtcccatgc atagatgaca cccggatatt    60
cactctggat aaaaccaagc acacccttta tataattttc aagtctggca agcatggtct   120
ctctgtcggt atagggaaat gactcgttat agtgctcaca gaaaaaccac ttcggtgtct   180
gattgtgcca caccagcgta tgaagccg                                     208
```

<210> SEQ ID NO 29
<211> LENGTH: 310
<212> TYPE: DNA
<213> ORGANISM: Hybrid
<220> FEATURE:
<221> NAME/KEY: misc_feature
<222> LOCATION: (1)...(310)
<223> OTHER INFORMATION: n = a, c, g, or t

<400> SEQUENCE: 29

```
aattcggctt gttgtagtcg ttgtagtaca gcttgcagtt tgaaggagcg tactttcttg    60
catatgtgaa cgctttctca ataaatgcgt tgctgccgta aacctgtacc caagggaaa   120
gcgccgttgc cgtacccgga actcttgctc cgccgttgtt acgtgttctg ttggagtcac   180
anaaaataca ctcgttgcag acatctaaag cttaaaggtt aatccgggat actgtgactg   240
ataggccgaa catatcttga agttaccttc cagtccnggt ccatacggaa tgctaccagc   300
ttcgccgtcc                                                          310
```

<210> SEQ ID NO 30
<211> LENGTH: 384
<212> TYPE: DNA
<213> ORGANISM: Hybrid
<220> FEATURE:
<221> NAME/KEY: misc_feature
<222> LOCATION: (1)...(384)
<223> OTHER INFORMATION: n = a, c, g, or t

<400> SEQUENCE: 30
aattcggctt gttgtantng ttgwwgaaga ngtggcagnt tgccggtgcc gcatcatggg    60
catattcaaa tgcctttgca atgaagctgt tgtcaccgta aacctgcacc cacgggact   120 tgccgtcatt gtaacccggc tcacgggcgc cgcctgcacc acgcgtacgc gcatcgctgt  180
cggagataca ctcgttgcag acgtcgtarg cgtanargtt cagcgtcnga tagttgttct  240
tgtacattgc aamcatattg tcaatgtanc ycttgangcg ctggttcatg acagtggant  300
tcacccactg accgccgtcc tggaaagtta tccttgaaan aaccagancg gartctggra  360
gtgccacncc ancgtrtgaa gccg                                          384

<210> SEQ ID NO 31
<211> LENGTH: 354
<212> TYPE: DNA
<213> ORGANISM: Hybrid
<220> FEATURE:
<221> NAME/KEY: misc_feature
<222> LOCATION: (1)...(354)
<223> OTHER INFORMATION: n = a, c, g, or t

<400> SEQUENCE: 31
aattcggctt catacgttgg tgtggcacaa tcagacgccc gtatggtttt ttaaggaaaa    60
ctgggaaaat gactggaacg cgcctgccgc ccccaaagaa atcctgctcg cccgcctgga   120
aaactatatc cgggatgtca tgcggcatgt gaatacctgt ttccccggtg tggtctacac   180
ctgggatgtg gtgaacgaag ccatcgaacc ggggcagggc ggtcccggcc tgttccggaa   240
ccgcaatccc tggtttgctt tcacaggcca ngatttcctg ccggctgcct tccgggcccc   300
cgcgaaaacn aagtcccggg acagaacctg tgctacaacg actacaacaa gccg         354

<210> SEQ ID NO 32
<211> LENGTH: 374
<212> TYPE: DNA
<213> ORGANISM: Hybrid
<220> FEATURE:
<221> NAME/KEY: misc_feature
<222> LOCATION: (1)...(374)
<223> OTHER INFORMATION: n = a, c, g, or t

<400> SEQUENCE: 32
aattcggctt catacgctgg tgtggcacag ccagactcct gactggttct tcaaggagaa    60
cttcagctca aacggtcagc tcgtatcaaa ggatataatg aatcagcgta tcgaaaacta   120
catcaagaac gtattcacaa tgctcaatgc agagtatcct acagttcagt tctatgctta   180
cgatgtagct aacgagtgta tggctgacag cagaaacggc ggtctcagac cggctggcat   240
gaatcagcag aacggcgaat ccccatggaa tcttatctac ggcgacaaca gctacctcga   300
tgtancattc aaggctgcta agaaattatg ctcctgctgg ctgcnaactt ttcttcaacg   360
actacaacaa gccg                                                     374

<210> SEQ ID NO 33
<211> LENGTH: 376
<212> TYPE: DNA
<213> ORGANISM: Hybrid
<220> FEATURE:
<221> NAME/KEY: misc_feature
<222> LOCATION: (1)...(376)
<223> OTHER INFORMATION: n = a, c, g, or t

<400> SEQUENCE: 33

```
aattcggctt catacgctgg tgtggcacag ccagactccc gagtggttct tcaaggagga      60
cttcgacgag aagaaggatt acgtttctcc cgaaaagatg aagaagcgta tggagaacta    120
catcaagagc ttcttcacaa cacttacaga gctctatccc gacgttgact tctatgcctg    180
cgacgttgta aacgangcat ggacagacga cggaaagccc cgtgaggcag gtcactgttc    240
acagtccaac aactacggcg cttccgactg ggttgctgta ttcggcgaca actcattcat    300
cgactacgct tcgagtatg caagaaagta tgctcccgan gctgcaagc tctactacaa      360
cgactacaac aagccg                                                     376
```

<210> SEQ ID NO 34
<211> LENGTH: 166
<212> TYPE: DNA
<213> ORGANISM: Hybrid

<400> SEQUENCE: 34

```
aattcggctt tgggatgtgg tgaacgaggc cttcaacgaa gacggttcac ggcgcagcga     60
cgttttccag aatgtgctcg gcaacggcta tatcgagcag gcattcagga ccgcgcgtgc   120
ggctgacccc aatgccaaac tgtgctacaa cgactacaac aagccg                  166
```

<210> SEQ ID NO 35
<211> LENGTH: 151
<212> TYPE: DNA
<213> ORGANISM: Hybrid

<400> SEQUENCE: 35

```
aattcggctt gttgtagtcg ttgttgaaca ggcgggtggt tgggtctacc tcatgagcaa     60
gttgatacca gtgcacaaca gcatcgaggc cgccgagggc atcataaacc tcgtggttat   120
ctaccggctc gttcaccaca tcccaaagcc g                                   151
```

<210> SEQ ID NO 36
<211> LENGTH: 166
<212> TYPE: DNA
<213> ORGANISM: Hybrid

<400> SEQUENCE: 36

```
aattcggctt gttgtagtcg ttgtagcaca gtttggcatt gggatctgta acccgtgcag     60
ctttgaatgc ctcttcaata tagctattgc caatcagccg ttggaagatt gaggcacgcc   120
gtgagccatt gtcttcgaag gcctcattca ccacatccca aagccg                  166
```

<210> SEQ ID NO 37
<211> LENGTH: 250
<212> TYPE: DNA
<213> ORGANISM: Hybrid

<400> SEQUENCE: 37

```
aattcggctt gttgtagtcg ttgwtgmaga gttttacatc ttttggacca tatttgcgag     60
ccagacgaca ggcctgacgg acgtagtcga tatcacccag atagtcctgc cagtagaaat   120
tatcgccgcc cacatcccat gtggcatctg gattaccatt aggattatac ttagcagagt   180
gttgtaataa gtagttgcct tgtccgtcat caccaccacc agagatcgcc tcrttcacca   240
catcccaaag                                                           250
```

<210> SEQ ID NO 38
<211> LENGTH: 247

```
<212> TYPE: DNA
<213> ORGANISM: Hybrid

<400> SEQUENCE: 38
aattcggctt tgggaygtgg tgaaygaggc gatagagctt aacgacaaga ccgaaaccgg      60
acttcgtaat tcatactggt atcaaataat cggtgacgat ttcatatatt acgcatttcg     120
ctatgcatat gacgcaagag aggaactgtg cgttaaatat gcggccgagt acggcattga     180
cccttcggac aaagaagcgc ttaaagccat ccgccccgct ttctgcaaca acgactacaa     240
caagccg                                                               247

<210> SEQ ID NO 39
<211> LENGTH: 238
<212> TYPE: DNA
<213> ORGANISM: Hybrid

<400> SEQUENCE: 39
aattcggctt tgggatgtgg tgaacgaggc tatctcgggt ggcgacagtg acggcgacgg      60
ttactacgac ctccagcatt ccgagggcta taagaacggc acttgggatg taggcggcga     120
tgccttctac tggcaggact acatgggcga cctggattac gtrcgtcagg cttgccgact     180
ggcccgcaaa tacggccctg aggatgtgaa gctytkcatc aacgactaca acaagccg      238

<210> SEQ ID NO 40
<211> LENGTH: 226
<212> TYPE: DNA
<213> ORGANISM: Hybrid

<400> SEQUENCE: 40
aattcggctt gttgtagtcg ttgatgcaca acagggcatt ggggtcggcc tcacgggcaa      60
actcgaaagc tttggcaatg aactcgtcgc cgcagagttt gtaatgacga ctctcacgat     120
aggggctggg agcctgacct ggacggcgtc cgaaaccgcc aaagccacca agccaccaa      180 agccgccacc gtcggaaatg gcctcgttca ctacatccca aagccg                    226

<210> SEQ ID NO 41
<211> LENGTH: 205
<212> TYPE: DNA
<213> ORGANISM: Hybrid

<400> SEQUENCE: 41
atctgcagaa attcggcttt gggacgtggt gaacgaggct atggccgacg acgttcgccg      60
ctcgccctgg aacccgaatc cgtcgcctta ccgcaactcg aaactctatc agttgtgcgg     120
tgatgagttc atcgctaaag cattccaatt cgcccgtgag gccgacccga acgcacaatt     180
gtgcatcaac gactacaaca agccg                                           205

<210> SEQ ID NO 42
<211> LENGTH: 235
<212> TYPE: DNA
<213> ORGANISM: Hybrid

<400> SEQUENCE: 42
aattcggctt gttgtagtcg ttgatgaaga gcttcatatc ctgtggacca tacttgcgag      60
ccagcttaac ggcagtacga acatagtcga tatcgcccag ataatcctgc cagaagaagc     120
tctcggttgc agccttttct ggatcttcct gatccttcag gtgctgcaaa gcatatacgc     180
cctcagcatc ggcatgtccg cttgagagtg cctcgttcac cacatcccaa agccg          235
```

<210> SEQ ID NO 43
<211> LENGTH: 244
<212> TYPE: DNA
<213> ORGANISM: Hybrid
<220> FEATURE:
<221> NAME/KEY: misc_feature
<222> LOCATION: (1)...(244)
<223> OTHER INFORMATION: n = a, c, g, or t

<400> SEQUENCE: 43

```
aattcggctt gttgtagtcg ttgatgaana gtttcaagtc ttccggttg cccttgaagt      60 gcttgcgcgc actcttaacc gcggtacgca cgtattcgan gtcgcccata tcgtcctgcc     120
aaaagaanag ccattctgca ctgaagtcgg gtcggtgttg cggctactgt tgtgctgaan    180
gggataattg ccctgcccat cgttgccgcc gccaganata cctcgttcac acgtcccaaa    240
gccg                                                                  244
```

<210> SEQ ID NO 44
<211> LENGTH: 212
<212> TYPE: DNA
<213> ORGANISM: Hybrid

<400> SEQUENCE: 44

```
aaattcggct tgttgtagtc gttgatgtac aggaccgggg ctttgccgta cttggcgcaa      60
gcctctgttg cataggcgaa tgcagcatca acccagtctt tggtgctcgg gtaataattg    120
ccccagacaa agtcgttggc agatgctccc tgggtgcgga atgccccgcc ggcaccgtct    180
gcaaaggtct cgttcaccac gtcccaaagc cg                                   212
```

<210> SEQ ID NO 45
<211> LENGTH: 190
<212> TYPE: DNA
<213> ORGANISM: Hybrid

<400> SEQUENCE: 45

```
aattcggctt gttgtagtcg ttgtagaaca gacctgcatt aggatcagcc tcgtgagcaa      60
actggaatgc cttgaggatg aactcgtcac cgcagagctg ataagcggtt gactgacgga    120
atgactgctc gtaaggaaca tcggggttgt tgccgtcgct cattgcctcg tttaccacgt    180
cccaaagccg                                                            190
```

<210> SEQ ID NO 46
<211> LENGTH: 234
<212> TYPE: DNA
<213> ORGANISM: Hybrid

<400> SEQUENCE: 46

```
aattcggctt gacgggggga cgtaygayat ctacgagacc acccgctaca acgaaccctc      60
catcatcggc accgccacct tcaaccagta ctggagcgtg cgccagtcca ggcgcaccgg    120
cggcaccatc accaccggca accacttcga cgcctgggcc agccacggca tgaacctggg    180
caccttcaac taccagatcc tggccaccga rggctaccaa tsctscggaa gccg           234
```

<210> SEQ ID NO 47
<211> LENGTH: 234
<212> TYPE: DNA
<213> ORGANISM: Hybrid

<400> SEQUENCE: 47

```
aattcggctt gacgggggra cgtacgacat ctacgagcac cagcaagtca accagccctc      60
```

| catccaaggc actgcgacct tcaaccagta ctggtccatc cgccagagca agcgttccag | 120 |
| cggcactgtg accactgcca accacttcaa tgcttgggcc aagttgggaa tgaacctggg | 180 |
| caacttcaac taccagattg tttccactga rggctaccag wcctscggaa gccg | 234 |

<210> SEQ ID NO 48
<211> LENGTH: 234
<212> TYPE: DNA
<213> ORGANISM: Hybrid

<400> SEQUENCE: 48

| aattcggctt gacgggggga cgtatgatat ctacaagcac caacaggtca atcagccatc | 60 |
| tattcagggc accgccacct tcaatcagta ctggtcgatt cgacagagca agcggaccag | 120 |
| cggcactgtc actacggcaa accactttaa tgcctgggct gctcttggca tgaatatggg | 180 |
| tgcattcaat taccagatcc tcgttactga gggctaccaa tctaccggaa gccg | 234 |

<210> SEQ ID NO 49
<211> LENGTH: 213
<212> TYPE: DNA
<213> ORGANISM: Hybrid

<400> SEQUENCE: 49

| aattcggctt gacgggggga cgtacgacat ttatgaaaca accgtgtca atcagccttc | 60 |
| cattatcggg atcgcaacct tcaagcaata ttggagtgta cgtcaaacga aacgtacaag | 120 |
| cggaacggtc tccgtcagtg cgcattttag aaaatgggaa agcttaggga tgccaatggg | 180 |
| gaaaatgtat gaaacggcat ttactgtaag ccg | 213 |

<210> SEQ ID NO 50
<211> LENGTH: 195
<212> TYPE: DNA
<213> ORGANISM: Hybrid

<400> SEQUENCE: 50

| aattcggctt tgggacgtgg tgaatgaggc aatggcagac aatgttcgtc ctaacccgtg | 60 |
| gaatcccaac ccctcgccct accgtgactc ccgccactac aaattgtgcg gcgacgagtt | 120 |
| catcgccaag gcattccaat tcgcaaggga agccgacccg aaggcacaat tgttcaacaa | 180 |
| gactacaaca agccg | 195 |

<210> SEQ ID NO 51
<211> LENGTH: 211
<212> TYPE: DNA
<213> ORGANISM: Hybrid

<400> SEQUENCE: 51

| aattcggctt gttgtagtcg ttgatgcaca ggaccggggc tttgccgtac ttggcgcaag | 60 |
| cctctgttgc ataggcgaat gcagcatcaa cccagtcttt ggtgctcggg taataattgc | 120 |
| cccaaacaaa gtcgttggca gatgctccct gggtgcggaa tgccccgccg gcaccgtctg | 180 |
| caaaggtctc gttcaccacg tcccaaagcc g | 211 |

<210> SEQ ID NO 52
<211> LENGTH: 240
<212> TYPE: DNA
<213> ORGANISM: Hybrid
<220> FEATURE:
<221> NAME/KEY: misc_feature
<222> LOCATION: (1)...(240)

-continued

```
<223> OTHER INFORMATION: n = a, c, g, or t

<400> SEQUENCE: 52
aattcggctt gacgggggga cgtacgacat ctacaagacc accagatacg aacagccctc        60
tatcgacggc acacagacct tcgaccagta ctggagcgta agacagtcca agccacaggg       120
cgagggcaag aagatagaag gtactatctc agtgtccaag cacttcgatg cgtggaaaaa       180
gtgcggcctt gagctcggaa atatgtatga agtanctctt actatcgaag ggctaagccg       240

<210> SEQ ID NO 53
<211> LENGTH: 229
<212> TYPE: DNA
<213> ORGANISM: Hybrid
<220> FEATURE:
<221> NAME/KEY: misc_feature
<222> LOCATION: (1)...(229)
<223> OTHER INFORMATION: n = a, c, g, or t

<400> SEQUENCE: 53
aattcccgga ggtttggcag ccttcaatag taagagcagc ttcatacatt aatcctaatt        60
tcattccttt gcttgtccaa gctttgaagt ggtcacttac agaaatagtt ccactagttt       120 tttttttcagt tctgacactc cagaattgtt taaatgtagc agtaccatca attgaaggtt       180
gattaattct gtcagtggta tanatatcat acgtcccccc atcaagccg                   229

<210> SEQ ID NO 54
<211> LENGTH: 234
<212> TYPE: DNA
<213> ORGANISM: Hybrid
<220> FEATURE:
<221> NAME/KEY: misc_feature
<222> LOCATION: (1)...(234)
<223> OTHER INFORMATION: n = a, c, g or t

<400> SEQUENCE: 54
aattcggctt gacgggggga cgtacgacat atacgagact actcgttaca accagccttc        60
aatcgaaggc aacactactt tccagcagta ctggagcgtt cgtacatcca agcgcaccag       120
cggtaccatt tccgtatccg agcactttaa ggcttgggaa cgcatgggta tgagatgcgg       180 aaaccttttat gagactgctt taactgttga gggctaccan accaccggaa gccg             234

<210> SEQ ID NO 55
<211> LENGTH: 1060
<212> TYPE: DNA
<213> ORGANISM: Humicola insolens
<220> FEATURE:
<221> NAME/KEY: CDS
<222> LOCATION: (10)...(927)
<221> NAME/KEY: mat_peptide
<222> LOCATION: (73)...(927)
<221> NAME/KEY: sig_peptide
<222> LOCATION: (10)...(72)

<400> SEQUENCE: 55 ggatccaag atg cgt tcc tcc ccc ctc ctc ccg tcc gcc gtt gtg gcc gcc        51
          Met Arg Ser Ser Pro Leu Leu Pro Ser Ala Val Val Ala Ala
                  -20             -15                 -10 ctg ccg gtg ttg gcc ctt gcc gct gat ggc agg tcc acc cgc tac tgg          99
Leu Pro Val Leu Ala Leu Ala Ala Asp Gly Arg Ser Thr Arg Tyr Trp
        -5                  1               5 gac tgc tgc aag cct tcg tgc ggc tgg gcc aag aag gct ccc gtg aac         147
Asp Cys Cys Lys Pro Ser Cys Gly Trp Ala Lys Lys Ala Pro Val Asn
    10              15                  20                  25
```

```
cag cct gtc ttt tcc tgc aac gcc aac ttc cag cgt atc acg gac ttc     195
Gln Pro Val Phe Ser Cys Asn Ala Asn Phe Gln Arg Ile Thr Asp Phe
         30                  35                  40 gac gcc aag tcc ggc tgc gag ccg ggc gtc gcc tac tcg tgc gcc         243
Asp Ala Lys Ser Gly Cys Glu Pro Gly Val Ala Tyr Ser Cys Ala
     45                  50                  55 gac cag acc cca tgg gct gtg aac gac gac ttc gcg ctc ggt ttt gct     291
Asp Gln Thr Pro Trp Ala Val Asn Asp Asp Phe Ala Leu Gly Phe Ala
         60                  65                  70 gcc acc tct att gcc ggc agc aat gag gcg ggc tgg tgc tgc gcc tgc     339
Ala Thr Ser Ile Ala Gly Ser Asn Glu Ala Gly Trp Cys Cys Ala Cys
 75                  80                  85 tac gag ctc acc ttc aca tcc ggt cct gtt gct ggc aag aag atg gtc     387
Tyr Glu Leu Thr Phe Thr Ser Gly Pro Val Ala Gly Lys Lys Met Val
 90                  95                  100                 105 gtc cag tcc acc agc act ggc ggt gat ctt ggc agc aac cac ttc gat     435
Val Gln Ser Thr Ser Thr Gly Gly Asp Leu Gly Ser Asn His Phe Asp
             110                 115                 120 ctc aac atc ccc ggc ggc ggc gtc ggc atc ttc gac gga tgc act ccc     483
Leu Asn Ile Pro Gly Gly Gly Val Gly Ile Phe Asp Gly Cys Thr Pro
             125                 130                 135 cag ttc ggc ggt ctg ccc ggc cag cgc tac ggc ggc atc tcg tcc cgc     531
Gln Phe Gly Gly Leu Pro Gly Gln Arg Tyr Gly Gly Ile Ser Ser Arg
         140                 145                 150 aac gag tgc gat cgg ttc ccc gac gcc ctc aag ccc ggc tgc tac tgg     579
Asn Glu Cys Asp Arg Phe Pro Asp Ala Leu Lys Pro Gly Cys Tyr Trp
 155                 160                 165 cgc ttc gac tgg ttc aag aac gcc gac aat ccg agc ttc agc ttc cgt     627
Arg Phe Asp Trp Phe Lys Asn Ala Asp Asn Pro Ser Phe Ser Phe Arg
170                 175                 180                 185 cag gtc cag tgc cca gcc gag ctc gtc gct cgc acc gga tgc cgc cgc     675
Gln Val Gln Cys Pro Ala Glu Leu Val Ala Arg Thr Gly Cys Arg Arg
             190                 195                 200 aac gac gac ggc aac ttc cct gcc gtc cag atc ccc tcc agc agc acc     723
Asn Asp Asp Gly Asn Phe Pro Ala Val Gln Ile Pro Ser Ser Ser Thr
             205                 210                 215 agc tct ccg gtc aac cag cct acc agc acc agc acg tcc acc tcc         771
Ser Ser Pro Val Asn Gln Pro Thr Ser Thr Ser Thr Ser Thr Ser
         220                 225                 230 acc acc tcg agc ccg cca gtc cag cct acg act ccc agc ggc tgc act     819
Thr Thr Ser Ser Pro Pro Val Gln Pro Thr Thr Pro Ser Gly Cys Thr
 235                 240                 245 gct gag agg tgg gct cag tgc ggc ggc aat ggc tgg agc ggc tgc acc     867
Ala Glu Arg Trp Ala Gln Cys Gly Gly Asn Gly Trp Ser Gly Cys Thr
250                 255                 260                 265 acc tgc gtc gct ggc agc act tgc acg aag att aat gac tgg tac cat     915
Thr Cys Val Ala Gly Ser Thr Cys Thr Lys Ile Asn Asp Trp Tyr His
             270                 275                 280 cag tgc ctg tag acgcagggca gcttgagggc cttactggtg gccgcaacga         967
Gln Cys Leu * aatgacactc ccaatcactg tattagttct tgtacataat ttcgtcatcc ctccagggat   1027
tgtcacataa atgcaatgag gaacaatgag tac                                1060

<210> SEQ ID NO 56
<211> LENGTH: 305
<212> TYPE: PRT
<213> ORGANISM: Humicola insolens
<220> FEATURE:
<221> NAME/KEY: SIGNAL
<222> LOCATION: (1)...(21)
```

```
<400> SEQUENCE: 56

Met Arg Ser Ser Pro Leu Leu Pro Ser Ala Val Val Ala Ala Leu Pro
    -20                 -15                 -10
Val Leu Ala Leu Ala Ala Asp Gly Arg Ser Thr Arg Tyr Trp Asp Cys
 -5              1                   5                       10
Cys Lys Pro Ser Cys Gly Trp Ala Lys Lys Ala Pro Val Asn Gln Pro
             15                  20                  25
Val Phe Ser Cys Asn Ala Asn Phe Gln Arg Ile Thr Asp Phe Asp Ala
             30                  35                  40
Lys Ser Gly Cys Glu Pro Gly Val Ala Tyr Ser Cys Ala Asp Gln
             45              50                  55
Thr Pro Trp Ala Val Asn Asp Asp Phe Ala Leu Gly Phe Ala Ala Thr
 60                  65                  70                  75
Ser Ile Ala Gly Ser Asn Glu Ala Gly Trp Cys Cys Ala Cys Tyr Glu
                 80                  85                  90
Leu Thr Phe Thr Ser Gly Pro Val Ala Gly Lys Lys Met Val Val Gln
             95                 100                 105
Ser Thr Ser Thr Gly Gly Asp Leu Gly Ser Asn His Phe Asp Leu Asn
            110                 115                 120
Ile Pro Gly Gly Val Gly Ile Phe Asp Gly Cys Thr Pro Gln Phe
125                 130                 135
Gly Gly Leu Pro Gly Gln Arg Tyr Gly Gly Ile Ser Ser Arg Asn Glu
140                 145                 150                 155
Cys Asp Arg Phe Pro Asp Ala Leu Lys Pro Gly Cys Tyr Trp Arg Phe
                160                 165                 170
Asp Trp Phe Lys Asn Ala Asp Asn Pro Ser Phe Ser Phe Arg Gln Val
            175                 180                 185
Gln Cys Pro Ala Glu Leu Val Ala Arg Thr Gly Cys Arg Arg Asn Asp
        190                 195                 200
Asp Gly Asn Phe Pro Ala Val Gln Ile Pro Ser Ser Ser Thr Ser Ser
    205                 210                 215
Pro Val Asn Gln Pro Thr Ser Thr Ser Thr Thr Ser Thr Ser Thr Thr
220                 225                 230                 235
Ser Ser Pro Pro Val Gln Pro Thr Thr Pro Ser Gly Cys Thr Ala Glu
                240                 245                 250
Arg Trp Ala Gln Cys Gly Gly Asn Gly Trp Ser Gly Cys Thr Thr Cys
            255                 260                 265
Val Ala Gly Ser Thr Cys Thr Lys Ile Asn Asp Trp Tyr His Gln Cys
            270                 275                 280
Leu

<210> SEQ ID NO 57
<211> LENGTH: 9
<212> TYPE: PRT
<213> ORGANISM: Prokaryotic
<220> FEATURE:
<221> NAME/KEY: UNSURE
<222> LOCATION: (1)...(9)
<223> OTHER INFORMATION: Xaa = Pro or Thr

<400> SEQUENCE: 57

Thr Arg Tyr Trp Asp Cys Cys Lys Xaa
 1               5

<210> SEQ ID NO 58
```

```
<211> LENGTH: 6
<212> TYPE: PRT
<213> ORGANISM: Prokaryotic
<220> FEATURE:
<221> NAME/KEY: UNSURE
<222> LOCATION: (1)...(6)
<223> OTHER INFORMATION: Xaa = Phe or Tyr

<400> SEQUENCE: 58

Trp Arg Xaa Asp Trp Phe
 1               5

<210> SEQ ID NO 59
<211> LENGTH: 42
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(42)
<223> OTHER INFORMATION: n = inosine

<400> SEQUENCE: 59
gctgatggca ggtccacnmc gntaytggga ytgytgyaaw mc                    42

<210> SEQ ID NO 60
<211> LENGTH: 29
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(29)
<223> OTHER INFORMATION: n = inosine

<400> SEQUENCE: 60
gtcggcgttc ttwaaccawt cwyanckcc                                   29

<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61
tggttyaaga acgccgacaa tccg                                        24

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
tagtcacgga catctgcgtc cgagatctcg                                  30

<210> SEQ ID NO 63
<211> LENGTH: 93
<212> TYPE: DNA
<213> ORGANISM: Artificial Sequence
<220> FEATURE:
<223> OTHER INFORMATION: Primer

<400> SEQUENCE: 63
cgggatccca tttatgatgg tcgcgtggtg gtctctattt ctgtacggcc ttcaggtcgc    60
```

-continued

```
ggcacctgct ttcgctgctg atggcaggtc cac                              93
```

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64

```
tagtcacgga catctgcgtc cgagatctcg                                  30
```

<210> SEQ ID NO 65
<211> LENGTH: 922
<212> TYPE: DNA
<213> ORGANISM: Hybrid
<220> FEATURE:
<221> NAME/KEY: CDS
<222> LOCATION: (1)...(922)

<400> SEQUENCE: 65

```
cca ttt atg atg gtc gcg tgg tgg tct cta ttt ctg tac ggc ctt cag     48
Pro Phe Met Met Val Ala Trp Trp Ser Leu Phe Leu Tyr Gly Leu Gln
 1               5                  10                  15 gtc gcg gca cct gct ttc gct gct gat ggc agg tcc acg cgg tac tgg     96
Val Ala Ala Pro Ala Phe Ala Ala Asp Gly Arg Ser Thr Arg Tyr Trp
             20                  25                  30 gat tgc tgt aag ccg tcg tgc tcg tgg ccc ggc aag gcg ctc gtg aac    144
Asp Cys Cys Lys Pro Ser Cys Ser Trp Pro Gly Lys Ala Leu Val Asn
         35                  40                  45 cag ccc gtc tac gcc cgc aac gca aac ttc cag cgc atc acc gac ccc    192
Gln Pro Val Tyr Ala Arg Asn Ala Asn Phe Gln Arg Ile Thr Asp Pro
     50                  55                  60 aac gcc aag tcc ggc tgc gat ggc ggc tcc gcc ttc tcc tgc gcc gac    240
Asn Ala Lys Ser Gly Cys Asp Gly Gly Ser Ala Phe Ser Cys Ala Asp
 65                  70                  75                  80 cag acc ccg tgg gcc gtg agc gac gac ttt gcc tac ggt ttc gcg gct    288
Gln Thr Pro Trp Ala Val Ser Asp Asp Phe Ala Tyr Gly Phe Ala Ala
                 85                  90                  95 acg gcg ctc gcc ggc cag tcc gag tct tcg tgg tgc tgt gcc tgc tac    336
Thr Ala Leu Ala Gly Gln Ser Glu Ser Ser Trp Cys Cys Ala Cys Tyr
            100                 105                 110 gaa ctc acc ttc act tcg ggc ccc gtt gct ggc aag aag atg gct gtc    384
Glu Leu Thr Phe Thr Ser Gly Pro Val Ala Gly Lys Lys Met Ala Val
        115                 120                 125 cag tcc acc agc act ggc ggt gac ctc ggt agc aac cac ttt gac ctc    432
Gln Ser Thr Ser Thr Gly Gly Asp Leu Gly Ser Asn His Phe Asp Leu
    130                 135                 140 aac atg cca ggt ggc ggt gtc ggc atc ttc gac ggc tgc tcg cct cag    480
Asn Met Pro Gly Gly Gly Val Gly Ile Phe Asp Gly Cys Ser Pro Gln
145                 150                 155                 160 gtt ggc ggt ctc gcc ggc cag cgc tat ggc ggc gtc tcg tcc cgc agc    528
Val Gly Gly Leu Ala Gly Gln Arg Tyr Gly Gly Val Ser Ser Arg Ser
                165                 170                 175 gaa tgc gac tcc ttc ccc gcg gca ctc aag ccc ggc tgc tac tgg cgc    576
Glu Cys Asp Ser Phe Pro Ala Ala Leu Lys Pro Gly Cys Tyr Trp Arg
            180                 185                 190 tac gac tgg ttt aag aac gcc gac aat ccg agc ttc agc ttc cgt cag    624
Tyr Asp Trp Phe Lys Asn Ala Asp Asn Pro Ser Phe Ser Phe Arg Gln
        195                 200                 205 gtc cag tgc cca gcc gag ctc gtc gct cgc acc gga tgc cgc cgc aac    672
Val Gln Cys Pro Ala Glu Leu Val Ala Arg Thr Gly Cys Arg Arg Asn
```

```
                 210                 215                 220
gac gac ggc aac ttc cct gcc gtc cag atc ccc tcc agc agc acc agc    720
Asp Asp Gly Asn Phe Pro Ala Val Gln Ile Pro Ser Ser Ser Thr Ser
225                 230                 235                 240 tct ccg gtc aac cag cct acc agc acc agc acc acg tcc acc tcc acc    768
Ser Pro Val Asn Gln Pro Thr Ser Thr Ser Thr Thr Ser Thr Ser Thr
                245                 250                 255 acc tcg agc ccg cca gtc cag cct acg act ccc agc ggc tgc act gct    816
Thr Ser Ser Pro Pro Val Gln Pro Thr Thr Pro Ser Gly Cys Thr Ala
                260                 265                 270 gag agg tgg gct cag tgc ggc ggc aat ggc tgg agc ggg tgc acc acc    864
Glu Arg Trp Ala Gln Cys Gly Gly Asn Gly Trp Ser Gly Cys Thr Thr
                275                 280                 285 tgc gtc gct ggc agc act tgc acg aag att aat gac tgg tac cat cag    912
Cys Val Ala Gly Ser Thr Cys Thr Lys Ile Asn Asp Trp Tyr His Gln
290                 295                 300 tgc ctg tag a                                                      922
Cys Leu  *
305
```

<210> SEQ ID NO 66
<211> LENGTH: 306
<212> TYPE: PRT
<213> ORGANISM: Hybrid

<400> SEQUENCE: 66

```
Pro Phe Met Met Val Ala Trp Trp Ser Leu Phe Leu Tyr Gly Leu Gln
 1               5                  10                  15

Val Ala Ala Pro Ala Phe Ala Ala Asp Gly Arg Ser Thr Arg Tyr Trp
                20                  25                  30

Asp Cys Cys Lys Pro Ser Cys Ser Trp Pro Gly Lys Ala Leu Val Asn
            35                  40                  45

Gln Pro Val Tyr Ala Arg Asn Ala Asn Phe Gln Arg Ile Thr Asp Pro
        50                  55                  60

Asn Ala Lys Ser Gly Cys Asp Gly Gly Ser Ala Phe Ser Cys Ala Asp
65                  70                  75                  80

Gln Thr Pro Trp Ala Val Ser Asp Asp Phe Ala Tyr Gly Phe Ala Ala
                85                  90                  95

Thr Ala Leu Ala Gly Gln Ser Glu Ser Ser Trp Cys Cys Ala Cys Tyr
            100                 105                 110

Glu Leu Thr Phe Thr Ser Gly Pro Val Ala Gly Lys Lys Met Ala Val
        115                 120                 125

Gln Ser Thr Ser Thr Gly Gly Asp Leu Gly Ser Asn His Phe Asp Leu
130                 135                 140

Asn Met Pro Gly Gly Gly Val Gly Ile Phe Asp Gly Cys Ser Pro Gln
145                 150                 155                 160

Val Gly Gly Leu Ala Gly Gln Arg Tyr Gly Gly Val Ser Ser Arg Ser
                165                 170                 175

Glu Cys Asp Ser Phe Pro Ala Ala Leu Lys Pro Gly Cys Tyr Trp Arg
            180                 185                 190

Tyr Asp Trp Phe Lys Asn Ala Asp Asn Pro Ser Phe Ser Phe Arg Gln
        195                 200                 205

Val Gln Cys Pro Ala Glu Leu Val Ala Arg Thr Gly Cys Arg Arg Asn
210                 215                 220

Asp Asp Gly Asn Phe Pro Ala Val Gln Ile Pro Ser Ser Ser Thr Ser
225                 230                 235                 240
```

```
Ser Pro Val Asn Gln Pro Thr Ser Thr Thr Ser Thr Ser Thr
            245                 250                 255

Thr Ser Ser Pro Pro Val Gln Pro Thr Thr Pro Ser Gly Cys Thr Ala
        260                 265                 270

Glu Arg Trp Ala Gln Cys Gly Gly Asn Gly Trp Ser Gly Cys Thr Thr
    275                 280                 285

Cys Val Ala Gly Ser Thr Cys Thr Lys Ile Asn Asp Trp Tyr His Gln
290                 295                 300

Cys Leu
305

<210> SEQ ID NO 67
<211> LENGTH: 919
<212> TYPE: DNA
<213> ORGANISM: Hybrid
<220> FEATURE:
<221> NAME/KEY: CDS
<222> LOCATION: (2)...(919)

<400> SEQUENCE: 67 c cca ttt atg atg gtc gcg tgg tgg tct cta ttt ctg tac ggc ctt cag      49
  Pro Phe Met Met Val Ala Trp Trp Ser Leu Phe Leu Tyr Gly Leu Gln
   1               5                  10                  15 gtc gcg gca cct gct ttc gct gct gat ggc agg tcc acg agg tac tgg      97
Val Ala Ala Pro Ala Phe Ala Ala Asp Gly Arg Ser Thr Arg Tyr Trp
            20                  25                  30 gat tgt tgt aag ccc tct tgc tcc tgg ggc gac aag gcc tcg gtc agc     145
Asp Cys Cys Lys Pro Ser Cys Ser Trp Gly Asp Lys Ala Ser Val Ser
        35                  40                  45 gcc ccc gtc ctg acc tgc gac aag aac gac aac ccc atc tcc gac gcc     193
Ala Pro Val Leu Thr Cys Asp Lys Asn Asp Asn Pro Ile Ser Asp Ala
    50                  55                  60 aac gcc gtg agc ggt tgc aac ggc ggc act tcc tac acc tgc agc aac     241
Asn Ala Val Ser Gly Cys Asn Gly Gly Thr Ser Tyr Thr Cys Ser Asn
65                  70                  75                  80 aac tcc ccg tgg gct gtc aac gac aac ctc gcc tat ggc ttt gcc gct     289
Asn Ser Pro Trp Ala Val Asn Asp Asn Leu Ala Tyr Gly Phe Ala Ala
                85                  90                  95 acc aag ctc tct gga ggc tcc gag tcc agc tgg tgc tgt gct tgc tac     337
Thr Lys Leu Ser Gly Gly Ser Glu Ser Ser Trp Cys Cys Ala Cys Tyr
            100                 105                 110 gct ctc acc ttt acg act ggc ccc gtg aag ggc aag acc atg gtc gta     385
Ala Leu Thr Phe Thr Thr Gly Pro Val Lys Gly Lys Thr Met Val Val
        115                 120                 125 cag tcc acc aac acc gga ggc gat ctc ggc gag aac cac ttc gat ctc     433
Gln Ser Thr Asn Thr Gly Gly Asp Leu Gly Glu Asn His Phe Asp Leu
    130                 135                 140 cag atg ccc ggc ggt ggt gtc ggc atc ttt gac ggc tgc agc tcc cag     481
Gln Met Pro Gly Gly Gly Val Gly Ile Phe Asp Gly Cys Ser Ser Gln
145                 150                 155                 160 tgg ggt ggc ctc ggc ggt gct cag tac ggc ggc atc tcg tcg cga agc     529
Trp Gly Gly Leu Gly Gly Ala Gln Tyr Gly Gly Ile Ser Ser Arg Ser
                165                 170                 175 gac tgc gac agc ttc ccc gag ctg ctc aag gac ggc tgc tac tgg cgc     577
Asp Cys Asp Ser Phe Pro Glu Leu Leu Lys Asp Gly Cys Tyr Trp Arg
            180                 185                 190 tac gac tgg ttc aag aac gcc gac aat ccg agc ttc agc ttc cgt cag     625
Tyr Asp Trp Phe Lys Asn Ala Asp Asn Pro Ser Phe Ser Phe Arg Gln
        195                 200                 205 gtc cag tgc cca gcc gag ctc gtc gct cgc acc gga tgc cgc cgc aac     673
```

```
Val Gln Cys Pro Ala Glu Leu Val Ala Arg Thr Gly Cys Arg Arg Asn
    210                 215                 220
```

| gac gac ggc aac ttc cct gcc gtc cag atc ccc tcc agc agc acc agc | 721 |
|---|---|
| Asp Asp Gly Asn Phe Pro Ala Val Gln Ile Pro Ser Ser Ser Thr Ser | |
| 225                 230                 235                 240 | |

| tct ccg gtc aac cag cct acc agc acc agc acc acg tcc acc tcc acc | 769 |
|---|---|
| Ser Pro Val Asn Gln Pro Thr Ser Thr Ser Thr Thr Ser Thr Ser Thr | |
|                 245                 250                 255 | |

| acc tcg agc ccg cca gtc cag cct acg act ccc agc ggc tgc act gct | 817 |
|---|---|
| Thr Ser Ser Pro Pro Val Gln Pro Thr Thr Pro Ser Gly Cys Thr Ala | |
|             260                 265                 270 | |

| gag agg tgg gct cag tgc ggc ggc aat ggc tgg agc ggc tgc acc acc | 865 |
|---|---|
| Glu Arg Trp Ala Gln Cys Gly Gly Asn Gly Trp Ser Gly Cys Thr Thr | |
|         275                 280                 285 | |

| tgc gtc gct ggc agc act tgc acg aag att aat gac tgg tac cat cag | 913 |
|---|---|
| Cys Val Ala Gly Ser Thr Cys Thr Lys Ile Asn Asp Trp Tyr His Gln | |
|     290                 295                 300 | |

| tgc ctg | 919 |
|---|---|
| Cys Leu | |
| 305 | |

```
<210> SEQ ID NO 68
<211> LENGTH: 306
<212> TYPE: PRT
<213> ORGANISM: Hybrid

<400> SEQUENCE: 68

Pro Phe Met Met Val Ala Trp Trp Ser Leu Phe Leu Tyr Gly Leu Gln
1               5                   10                  15

Val Ala Ala Pro Ala Phe Ala Ala Asp Gly Arg Ser Thr Arg Tyr Trp
                20                  25                  30

Asp Cys Cys Lys Pro Ser Cys Ser Trp Gly Asp Lys Ala Ser Val Ser
            35                  40                  45

Ala Pro Val Leu Thr Cys Asp Lys Asn Asp Asn Pro Ile Ser Asp Ala
        50                  55                  60

Asn Ala Val Ser Gly Cys Asn Gly Gly Thr Ser Tyr Thr Cys Ser Asn
65                  70                  75                  80

Asn Ser Pro Trp Ala Val Asn Asp Asn Leu Ala Tyr Gly Phe Ala Ala
                85                  90                  95

Thr Lys Leu Ser Gly Gly Ser Glu Ser Ser Trp Cys Cys Ala Cys Tyr
            100                 105                 110

Ala Leu Thr Phe Thr Thr Gly Pro Val Lys Gly Lys Thr Met Val Val
        115                 120                 125

Gln Ser Thr Asn Thr Gly Gly Asp Leu Gly Glu Asn His Phe Asp Leu
    130                 135                 140

Gln Met Pro Gly Gly Gly Val Gly Ile Phe Asp Gly Cys Ser Ser Gln
145                 150                 155                 160

Trp Gly Gly Leu Gly Gly Ala Gln Tyr Gly Gly Ile Ser Ser Arg Ser
                165                 170                 175

Asp Cys Asp Ser Phe Pro Glu Leu Leu Lys Asp Gly Cys Tyr Trp Arg
            180                 185                 190

Tyr Asp Trp Phe Lys Asn Ala Asp Asn Pro Ser Phe Ser Phe Arg Gln
        195                 200                 205

Val Gln Cys Pro Ala Glu Leu Val Ala Arg Thr Gly Cys Arg Arg Asn
    210                 215                 220

Asp Asp Gly Asn Phe Pro Ala Val Gln Ile Pro Ser Ser Ser Thr Ser
225                 230                 235                 240
```

```
Ser Pro Val Asn Gln Pro Thr Ser Thr Ser Thr Ser Thr
            245                 250                 255

Thr Ser Ser Pro Pro Val Gln Pro Thr Thr Pro Ser Gly Cys Thr Ala
            260                 265                 270

Glu Arg Trp Ala Gln Cys Gly Gly Asn Gly Trp Ser Gly Cys Thr Thr
        275                 280                 285

Cys Val Ala Gly Ser Thr Cys Thr Lys Ile Asn Asp Trp Tyr His Gln
    290                 295                 300

Cys Leu
305

<210> SEQ ID NO 69
<211> LENGTH: 924
<212> TYPE: DNA
<213> ORGANISM: Hybrid
<220> FEATURE:
<221> NAME/KEY: CDS
<222> LOCATION: (1)...(924)

<400> SEQUENCE: 69 cca ttt atg atg gtc gcg tgg tgg tct cta ttt ctg tac ggc ctt cag       48
Pro Phe Met Met Val Ala Trp Trp Ser Leu Phe Leu Tyr Gly Leu Gln
1               5                   10                  15 gtc gcg gca cct gct ttc gct gct gat ggc agg tcc acg agg tac tgg       96
Val Ala Ala Pro Ala Phe Ala Ala Asp Gly Arg Ser Thr Arg Tyr Trp
            20                  25                  30 gat tgc tgc aag ccc tct tgc tct tgg ggc gga aag gct gct gtc agc      144
Asp Cys Cys Lys Pro Ser Cys Ser Trp Gly Gly Lys Ala Ala Val Ser
        35                  40                  45 gcc cct gct ttg acc tgt gac aag aag gac aac ccc atc tca aac ctg      192
Ala Pro Ala Leu Thr Cys Asp Lys Lys Asp Asn Pro Ile Ser Asn Leu
    50                  55                  60 aac gct gtc aac ggt tgt gag ggt ggt ggt tct gcc ttc gcc tgc acc      240
Asn Ala Val Asn Gly Cys Glu Gly Gly Gly Ser Ala Phe Ala Cys Thr
65                  70                  75                  80 aac tac tct cct tgg gcg gtc aat gac aac ctt gcc tac ggc ttc gct      288
Asn Tyr Ser Pro Trp Ala Val Asn Asp Asn Leu Ala Tyr Gly Phe Ala
                85                  90                  95 gca acc aag ctt gcc ggt ggc tcc gag ggt agc tgg tgc tgt gct tgc      336
Ala Thr Lys Leu Ala Gly Gly Ser Glu Gly Ser Trp Cys Cys Ala Cys
            100                 105                 110 tac gca ctt acc ttc acc acc ggt ccc gtc aag ggt aag acc atg gtc      384
Tyr Ala Leu Thr Phe Thr Thr Gly Pro Val Lys Gly Lys Thr Met Val
        115                 120                 125 gtc cag tcc acc aac act gga ggc gac ctc ggt gac aac cac ttc gat      432
Val Gln Ser Thr Asn Thr Gly Gly Asp Leu Gly Asp Asn His Phe Asp
    130                 135                 140 ctt atg atg cct ggt ggc ggt gtt gga atc ttc gac ggt tgc act tct      480
Leu Met Met Pro Gly Gly Gly Val Gly Ile Phe Asp Gly Cys Thr Ser
145                 150                 155                 160 cag ttc ggc aag gct ctc ggt ggt gcc cag tac ggt ggc atc tcc tcc      528
Gln Phe Gly Lys Ala Leu Gly Gly Ala Gln Tyr Gly Gly Ile Ser Ser
                165                 170                 175 cga agc gag tgc gac agc ttc cct gag act ctc aag gac ggt tgc cat      576
Arg Ser Glu Cys Asp Ser Phe Pro Glu Thr Leu Lys Asp Gly Cys His
            180                 185                 190 tgg cgc ttc gac tgg ttc aag aac gcc gac aat ccg agc ttc agc ttc      624
Trp Arg Phe Asp Trp Phe Lys Asn Ala Asp Asn Pro Ser Phe Ser Phe
        195                 200                 205
```

```
cgt cag gtc cag tgc cca gcc gag ctc gtc gct cgc acc gga tgc cgc        672
Arg Gln Val Gln Cys Pro Ala Glu Leu Val Ala Arg Thr Gly Cys Arg
    210                 215                 220 cgc aac gac gac ggc aac ttc cct gcc gtc cag atc ccc tcc agc agc        720
Arg Asn Asp Asp Gly Asn Phe Pro Ala Val Gln Ile Pro Ser Ser Ser
225                 230                 235                 240 acc agc tct ccg gtc aac cag cct acc agc acc agc acc acg tcc acc        768
Thr Ser Ser Pro Val Asn Gln Pro Thr Ser Thr Ser Thr Thr Ser Thr
                245                 250                 255 tcc acc acc tcg agc ccg cca gtc cag cct acg act ccc agc ggc tgc        816
Ser Thr Thr Ser Ser Pro Pro Val Gln Pro Thr Thr Pro Ser Gly Cys
            260                 265                 270 act gct gag agg tgg gct cag tgc ggc ggc aat ggc tgg agc ggc tgc        864
Thr Ala Glu Arg Trp Ala Gln Cys Gly Gly Asn Gly Trp Ser Gly Cys
        275                 280                 285 acc acc tgc gtc gct ggc agc act tgc acg aag att aat gac tgg tac        912
Thr Thr Cys Val Ala Gly Ser Thr Cys Thr Lys Ile Asn Asp Trp Tyr
    290                 295                 300 cat cag tgc ctg                                                        924
His Gln Cys Leu
305

<210> SEQ ID NO 70
<211> LENGTH: 308
<212> TYPE: PRT
<213> ORGANISM: Hybrid

<400> SEQUENCE: 70

Pro Phe Met Met Val Ala Trp Trp Ser Leu Phe Leu Tyr Gly Leu Gln
1               5                   10                  15

Val Ala Ala Pro Ala Phe Ala Ala Asp Gly Arg Ser Thr Arg Tyr Trp
                20                  25                  30

Asp Cys Cys Lys Pro Ser Cys Ser Trp Gly Gly Lys Ala Ala Val Ser
            35                  40                  45

Ala Pro Ala Leu Thr Cys Asp Lys Lys Asp Asn Pro Ile Ser Asn Leu
        50                  55                  60

Asn Ala Val Asn Gly Cys Glu Gly Gly Gly Ser Ala Phe Ala Cys Thr
65                  70                  75                  80

Asn Tyr Ser Pro Trp Ala Val Asn Asp Asn Leu Ala Tyr Gly Phe Ala
                85                  90                  95

Ala Thr Lys Leu Ala Gly Gly Ser Glu Gly Ser Trp Cys Cys Ala Cys
            100                 105                 110

Tyr Ala Leu Thr Phe Thr Thr Gly Pro Val Lys Gly Lys Thr Met Val
        115                 120                 125

Val Gln Ser Thr Asn Thr Gly Gly Asp Leu Gly Asp Asn His Phe Asp
    130                 135                 140

Leu Met Met Pro Gly Gly Gly Val Gly Ile Phe Asp Gly Cys Thr Ser
145                 150                 155                 160

Gln Phe Gly Lys Ala Leu Gly Gly Ala Gln Tyr Gly Gly Ile Ser Ser
                165                 170                 175

Arg Ser Glu Cys Asp Ser Phe Pro Glu Thr Leu Lys Asp Gly Cys His
            180                 185                 190

Trp Arg Phe Asp Trp Phe Lys Asn Ala Asp Asn Pro Ser Phe Ser Phe
        195                 200                 205

Arg Gln Val Gln Cys Pro Ala Glu Leu Val Ala Arg Thr Gly Cys Arg
    210                 215                 220

Arg Asn Asp Asp Gly Asn Phe Pro Ala Val Gln Ile Pro Ser Ser Ser
```

```
              225                 230                 235                 240
Thr Ser Ser Pro Val Asn Gln Pro Thr Ser Thr Ser Thr Thr Ser Thr
                        245                 250                 255
Ser Thr Thr Ser Ser Pro Pro Val Gln Pro Thr Thr Pro Ser Gly Cys
                260                 265                 270
Thr Ala Glu Arg Trp Ala Gln Cys Gly Gly Asn Gly Trp Ser Gly Cys
            275                 280                 285
Thr Thr Cys Val Ala Gly Ser Thr Cys Thr Lys Ile Asn Asp Trp Tyr
        290                 295                 300
His Gln Cys Leu
305

<210> SEQ ID NO 71
<211> LENGTH: 912
<212> TYPE: DNA
<213> ORGANISM: Hybrid
<220> FEATURE:
<221> NAME/KEY: CDS
<222> LOCATION: (1)...(912)

<400> SEQUENCE: 71 atg atg gtc gcg tgg tgg tct cta ttt ctg tac ggc ctt cag gtc gcg    48
Met Met Val Ala Trp Trp Ser Leu Phe Leu Tyr Gly Leu Gln Val Ala
1               5                  10                  15 gca cct gct ttc gct gct gat ggc agg tcc acg agg tat tgg gat tgt    96
Ala Pro Ala Phe Ala Ala Asp Gly Arg Ser Thr Arg Tyr Trp Asp Cys
            20                  25                  30 tgc aag ccg tca tgt gct tgg tcc ggc aag gcc tca gtg tca tct ccc   144
Cys Lys Pro Ser Cys Ala Trp Ser Gly Lys Ala Ser Val Ser Ser Pro
        35                  40                  45 gtg cga acc tgt gac gca aac aac tcg ccg ctg tcc gac gtc gac gca   192
Val Arg Thr Cys Asp Ala Asn Asn Ser Pro Leu Ser Asp Val Asp Ala
    50                  55                  60 aag agt gcg tgc gat gga ggc gtt gct tac act tgt tca aac aac gcg   240
Lys Ser Ala Cys Asp Gly Gly Val Ala Tyr Thr Cys Ser Asn Asn Ala
65                  70                  75                  80 cct tgg gct gtt aac gat aac ctc tct tat ggt ttc gcg gcc aca gct   288
Pro Trp Ala Val Asn Asp Asn Leu Ser Tyr Gly Phe Ala Ala Thr Ala
                85                  90                  95 atc aat ggc ggc agc gag tct agc tgg tgc tgt gca tgc tac aag ttg   336
Ile Asn Gly Gly Ser Glu Ser Ser Trp Cys Cys Ala Cys Tyr Lys Leu
            100                 105                 110 act ttc acg agc gga cct gct tct gga aag gtc atg gtc gtt caa tca   384
Thr Phe Thr Ser Gly Pro Ala Ser Gly Lys Val Met Val Val Gln Ser
        115                 120                 125 acc aac acc ggg tac gat ctc tct aac aac cac ttt gac att ctt atg   432
Thr Asn Thr Gly Tyr Asp Leu Ser Asn Asn His Phe Asp Ile Leu Met
    130                 135                 140 cca ggt ggc ggt gtt gga gcg ttc gac ggc tgc tct agg cag tac ggc   480
Pro Gly Gly Gly Val Gly Ala Phe Asp Gly Cys Ser Arg Gln Tyr Gly
145                 150                 155                 160 agc atc cct ggg gag cga tat ggg ggt gtc aca tca agg gac caa tgc   528
Ser Ile Pro Gly Glu Arg Tyr Gly Gly Val Thr Ser Arg Asp Gln Cys
                165                 170                 175 gac caa atg cca agt gca ctc aag cag ggc tgc tat tgg cgc ttc gat   576
Asp Gln Met Pro Ser Ala Leu Lys Gln Gly Cys Tyr Trp Arg Phe Asp
            180                 185                 190 tgg ttc aag aac gcc gac aat ccg agc ttc agc ttc cgt cag gtc cag   624
Trp Phe Lys Asn Ala Asp Asn Pro Ser Phe Ser Phe Arg Gln Val Gln
        195                 200                 205
```

```
tgc cca gcc gag ctc gtc gct cgc acc gga tgc cgc cgc aac gac gac      672
Cys Pro Ala Glu Leu Val Ala Arg Thr Gly Cys Arg Arg Asn Asp Asp
    210                 215                 220 ggc aac ttc cct gcc gtc cag atc ccc tcc agc agc acc agc tct ccg      720
Gly Asn Phe Pro Ala Val Gln Ile Pro Ser Ser Ser Thr Ser Ser Pro
225                 230                 235                 240 gtc aac cag cct acc agc acc agc acc acg tcc acc tcc acc acc tcg      768
Val Asn Gln Pro Thr Ser Thr Ser Thr Thr Ser Thr Ser Thr Thr Ser
                245                 250                 255 agc ccg cca gtc cag cct acg act ccc agc ggc tgc act gct gag agg      816
Ser Pro Pro Val Gln Pro Thr Thr Pro Ser Gly Cys Thr Ala Glu Arg
            260                 265                 270 tgg gct cag tgc ggc ggc aat ggc tgg agc ggc tgc acc acc tgc gtc      864
Trp Ala Gln Cys Gly Gly Asn Gly Trp Ser Gly Cys Thr Thr Cys Val
        275                 280                 285 gct ggc agc act tgc acg aag att aat gac tgg tac cat cag tgc ctg      912
Ala Gly Ser Thr Cys Thr Lys Ile Asn Asp Trp Tyr His Gln Cys Leu
    290                 295                 300

<210> SEQ ID NO 72
<211> LENGTH: 304
<212> TYPE: PRT
<213> ORGANISM: Hybrid

<400> SEQUENCE: 72

Met Met Val Ala Trp Trp Ser Leu Phe Leu Tyr Gly Leu Gln Val Ala
1               5                   10                  15

Ala Pro Ala Phe Ala Ala Asp Gly Arg Ser Thr Arg Tyr Trp Asp Cys
            20                  25                  30

Cys Lys Pro Ser Cys Ala Trp Ser Gly Lys Ala Ser Val Ser Ser Pro
        35                  40                  45

Val Arg Thr Cys Asp Ala Asn Asn Ser Pro Leu Ser Asp Val Asp Ala
    50                  55                  60

Lys Ser Ala Cys Asp Gly Gly Val Ala Tyr Thr Cys Ser Asn Asn Ala
65                  70                  75                  80

Pro Trp Ala Val Asn Asp Asn Leu Ser Tyr Gly Phe Ala Ala Thr Ala
                85                  90                  95

Ile Asn Gly Gly Ser Glu Ser Ser Trp Cys Cys Ala Cys Tyr Lys Leu
            100                 105                 110

Thr Phe Thr Ser Gly Pro Ala Ser Gly Lys Val Met Val Val Gln Ser
        115                 120                 125

Thr Asn Thr Gly Tyr Asp Leu Ser Asn Asn His Phe Asp Ile Leu Met
    130                 135                 140

Pro Gly Gly Gly Val Gly Ala Phe Asp Gly Cys Ser Arg Gln Tyr Gly
145                 150                 155                 160

Ser Ile Pro Gly Glu Arg Tyr Gly Gly Val Thr Ser Arg Asp Gln Cys
                165                 170                 175

Asp Gln Met Pro Ser Ala Leu Lys Gln Gly Cys Tyr Trp Arg Phe Asp
            180                 185                 190

Trp Phe Lys Asn Ala Asp Asn Pro Ser Phe Ser Phe Arg Gln Val Gln
        195                 200                 205

Cys Pro Ala Glu Leu Val Ala Arg Thr Gly Cys Arg Arg Asn Asp Asp
    210                 215                 220

Gly Asn Phe Pro Ala Val Gln Ile Pro Ser Ser Ser Thr Ser Ser Pro
225                 230                 235                 240

Val Asn Gln Pro Thr Ser Thr Ser Thr Thr Ser Thr Ser Thr Thr Ser
```

```
                 245                 250                 255
Ser Pro Pro Val Gln Pro Thr Thr Pro Ser Gly Cys Thr Ala Glu Arg
            260                 265                 270

Trp Ala Gln Cys Gly Gly Asn Gly Trp Ser Gly Cys Thr Thr Cys Val
        275                 280                 285

Ala Gly Ser Thr Cys Thr Lys Ile Asn Asp Trp Tyr His Gln Cys Leu
    290                 295                 300

<210> SEQ ID NO 73
<211> LENGTH: 922
<212> TYPE: DNA
<213> ORGANISM: Hybrid
<220> FEATURE:
<221> NAME/KEY: CDS
<222> LOCATION: (2)...(922)

<400> SEQUENCE: 73 c cca ttt atg atg gtc gcg tgg tgg tct cta ttt ctg tac ggc ctt cag      49
  Pro Phe Met Met Val Ala Trp Trp Ser Leu Phe Leu Tyr Gly Leu Gln
    1               5                  10                  15 gtc gcg gca cct gct ttc gct gct gat ggc agg tcc acg cgg tat tgg        97
Val Ala Ala Pro Ala Phe Ala Ala Asp Gly Arg Ser Thr Arg Tyr Trp
                20                  25                  30 gat tgc tgt aag ccc agc tgc tcc tgg ccc gac aag gcc ccc gta ggt       145
Asp Cys Cys Lys Pro Ser Cys Ser Trp Pro Asp Lys Ala Pro Val Gly
            35                  40                  45 tcc ccc gta ggc acc tgc gac gcc ggc aac agc ccc ctc ggc gac ccc       193
Ser Pro Val Gly Thr Cys Asp Ala Gly Asn Ser Pro Leu Gly Asp Pro
        50                  55                  60 ctg gcc aag tct ggc tgc gag ggc ggc ccg tcg tac acg tgc gcc aac       241
Leu Ala Lys Ser Gly Cys Glu Gly Gly Pro Ser Tyr Thr Cys Ala Asn
 65                  70                  75                  80 tac cag ccg tgg gcg gtc aac gac cag ctg gcc tac ggc ttc gcg gcc       289
Tyr Gln Pro Trp Ala Val Asn Asp Gln Leu Ala Tyr Gly Phe Ala Ala
                    85                  90                  95 acg gcc atc aac ggc ggc acc gag gac tcg tgg tgc tgc gcc tgc tac       337
Thr Ala Ile Asn Gly Gly Thr Glu Asp Ser Trp Cys Cys Ala Cys Tyr
                100                 105                 110 aag ctc acc ttc acc gac ggc ccg gcc tcg ggc aag acc atg atc gtc       385
Lys Leu Thr Phe Thr Asp Gly Pro Ala Ser Gly Lys Thr Met Ile Val
            115                 120                 125 cag tcc acc aac acg ggc ggc gac ctg tcc gac aac cac ttc gac ctg       433
Gln Ser Thr Asn Thr Gly Gly Asp Leu Ser Asp Asn His Phe Asp Leu
        130                 135                 140 ctc atc ccc ggc ggc ggc gtc ggc atc ttc gac ggc tgc acc tcc cag       481
Leu Ile Pro Gly Gly Gly Val Gly Ile Phe Asp Gly Cys Thr Ser Gln
145                 150                 155                 160 tac ggc cag gcc ctg ccc ggc gcc cag tac ggc ggc gtc agc tcc cgc       529
Tyr Gly Gln Ala Leu Pro Gly Ala Gln Tyr Gly Gly Val Ser Ser Arg
                    165                 170                 175 gcc gag tgc gac cag atg ccc gag gcc atc aag gcc ggc tgc cag tgg       577
Ala Glu Cys Asp Gln Met Pro Glu Ala Ile Lys Ala Gly Cys Gln Trp
                180                 185                 190 cgc tac gat tgg ttt aag aac gcc gac aat ccg agc ttc agc ttc cgt       625
Arg Tyr Asp Trp Phe Lys Asn Ala Asp Asn Pro Ser Phe Ser Phe Arg
            195                 200                 205 cag gtc cag tgc cca gcc gag ctc gtc gct cgc acc gga tgc cgc cgc       673
Gln Val Gln Cys Pro Ala Glu Leu Val Ala Arg Thr Gly Cys Arg Arg
        210                 215                 220 aac gac gac ggc aac ttc cct gcc gtc cag atc ccc tcc agc agc acc       721
```

| | | | | | | | | | | | | |
|---|---|---|---|---|---|---|---|---|---|---|---|---|
|Asn|Asp|Asp|Gly|Asn|Phe|Pro|Ala|Val|Gln|Ile|Pro|Ser|Ser|Ser|Thr|
|225| | | | |230| | | | |235| | | | |240|

```
agc tct ccg gtc aac cag cct acc agc acc agc acc acg tcc acc tcc      769
Ser Ser Pro Val Asn Gln Pro Thr Ser Thr Ser Thr Thr Ser Thr Ser
            245                 250                 255 acc acc tcg agc ccg cca gtc cag cct acg act ccc agc ggc tgc act      817
Thr Thr Ser Ser Pro Pro Val Gln Pro Thr Thr Pro Ser Gly Cys Thr
            260                 265                 270 gct gag agg tgg gct cag tgc ggc ggc aat ggc tgg agc ggc tgc acc      865
Ala Glu Arg Trp Ala Gln Cys Gly Gly Asn Gly Trp Ser Gly Cys Thr
            275                 280                 285 acc tgc gtc gct ggc agc act tgc acg aag att aat gac tgg tac cat      913
Thr Cys Val Ala Gly Ser Thr Cys Thr Lys Ile Asn Asp Trp Tyr His
    290                 295                 300 cag tgc ctg                                                          922
Gln Cys Leu
305

<210> SEQ ID NO 74
<211> LENGTH: 307
<212> TYPE: PRT
<213> ORGANISM: Hybrid

<400> SEQUENCE: 74

Pro Phe Met Met Val Ala Trp Trp Ser Leu Phe Leu Tyr Gly Leu Gln
1               5                   10                  15

Val Ala Ala Pro Ala Phe Ala Ala Asp Gly Arg Ser Thr Arg Tyr Trp
            20                  25                  30

Asp Cys Cys Lys Pro Ser Cys Ser Trp Pro Asp Lys Ala Pro Val Gly
        35                  40                  45

Ser Pro Val Gly Thr Cys Asp Ala Gly Asn Ser Pro Leu Gly Asp Pro
    50                  55                  60

Leu Ala Lys Ser Gly Cys Glu Gly Gly Pro Ser Tyr Thr Cys Ala Asn
65                  70                  75                  80

Tyr Gln Pro Trp Ala Val Asn Asp Gln Leu Ala Tyr Gly Phe Ala Ala
                85                  90                  95

Thr Ala Ile Asn Gly Gly Thr Glu Asp Ser Trp Cys Cys Ala Cys Tyr
            100                 105                 110

Lys Leu Thr Phe Thr Asp Gly Pro Ala Ser Gly Lys Thr Met Ile Val
        115                 120                 125

Gln Ser Thr Asn Thr Gly Gly Asp Leu Ser Asp Asn His Phe Asp Leu
    130                 135                 140

Leu Ile Pro Gly Gly Gly Val Gly Ile Phe Asp Gly Cys Thr Ser Gln
145                 150                 155                 160

Tyr Gly Gln Ala Leu Pro Gly Ala Gln Tyr Gly Gly Val Ser Ser Arg
                165                 170                 175

Ala Glu Cys Asp Gln Met Pro Glu Ala Ile Lys Ala Gly Cys Gln Trp
            180                 185                 190

Arg Tyr Asp Trp Phe Lys Asn Ala Asp Asn Pro Ser Phe Ser Phe Arg
        195                 200                 205

Gln Val Gln Cys Pro Ala Glu Leu Val Ala Arg Thr Gly Cys Arg Arg
    210                 215                 220

Asn Asp Asp Gly Asn Phe Pro Ala Val Gln Ile Pro Ser Ser Ser Thr
225                 230                 235                 240

Ser Ser Pro Val Asn Gln Pro Thr Ser Thr Ser Thr Thr Ser Thr Ser
                245                 250                 255
```

-continued

```
Thr Thr Ser Ser Pro Pro Val Gln Pro Thr Thr Pro Ser Gly Cys Thr
            260             265                 270

Ala Glu Arg Trp Ala Gln Cys Gly Gly Asn Gly Trp Ser Gly Cys Thr
            275             280                 285

Thr Cys Val Ala Gly Ser Thr Cys Thr Lys Ile Asn Asp Trp Tyr His
    290             295             300

Gln Cys Leu
305
```